(12) United States Patent
Stowell et al.

(10) Patent No.: US 12,358,952 B2
(45) Date of Patent: Jul. 15, 2025

(54) COMPOSITIONS AND METHODS OF SYNTHESIZING SHAPE SHIFTING CYCLIC PEPTIDES (Sscp) AND THEIR USE IN THE IDENTIFICATION OF NOVEL THERAPEUTIC COMPOUNDS

(71) Applicant: The Regents of the University of Colorado, Denver, CO (US)

(72) Inventors: Michael Stowell, Boulder, CO (US); William Old, Boulder, CO (US); Brady Worrell, Englewood, CO (US); John Mayer, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 18/272,674

(22) PCT Filed: Jan. 19, 2022

(86) PCT No.: PCT/US2022/012880
§ 371 (c)(1),
(2) Date: Jul. 17, 2023

(87) PCT Pub. No.: WO2022/159430
PCT Pub. Date: Jul. 28, 2022

(65) Prior Publication Data
US 2024/0158443 A1   May 16, 2024

Related U.S. Application Data

(60) Provisional application No. 63/139,080, filed on Jan. 19, 2021.

(51) Int. Cl.
   *C07K 7/56*   (2006.01)
   *C07K 1/00*   (2006.01)
   *C07K 1/04*   (2006.01)
   *G16B 35/10*  (2019.01)

(52) U.S. Cl.
   CPC ............ *C07K 7/56* (2013.01); *C07K 1/006* (2013.01); *C07K 1/04* (2013.01); *G16B 35/10* (2019.02)

(58) Field of Classification Search
   None
   See application file for complete search history.

(56) References Cited

U.S. PATENT DOCUMENTS

| 3,798,329 A | 3/1974 | Huebner |
| 2020/0023081 A1* | 1/2020 | Chen ............... A61K 49/0056 |

OTHER PUBLICATIONS

Sannigrah, Achintai et al, "The bright and dark side of protein conformational switches and the unifying forces of infection." Comm. Biol. (2020) 3:382.*
Yahiaoui et al. "Synthesis and Analysis of Substituted Bullvalenes" Angewandte Chemie International Edition. Jan. 5, 2018 (Jan. 5, 2018) vol. 57, p. 2570-2574; p. 2572, Scheme 3, p. 2573, Figure 2.
Patel et al. "Boronate Ester Bullvalenes" Journal of the American Chemical Society. Feb. 10, 2020 (Feb. 10, 2020) vol. 142, p. 3680-3685; p. 3681, Scheme 1.
Ferrer et al. "Synthesis of Barbaralones and Bullvalenes Made Easy by Gold Catalysis" Angewandte Chemie International Edition. Aug. 19, 2016 (Aug. 19, 2016); vol. 55, p. 11178-11182; p. 11181, Scheme 4.
Platts "Quantum chemical molecular dynamics and metadynamics simulation of aluminium binding to amyloid-beta and related peptides" Royal Society Open Science. Feb. 5, 2020 (Feb. 5, 2020), vol. 7, p. 1-9; entire document.
International Search Report and Written Opinion with mailing date of Jun. 6, 2022, 15 pages.

\* cited by examiner

*Primary Examiner* — Fred H Reynolds
(74) *Attorney, Agent, or Firm* — Berg Hill Greenleaf Ruscitti LLP

(57) ABSTRACT

The invention described herein includes a novel platform for the development of novel shapeshifting drug-like compounds that overcome physical mass limitations as they possess the ability to interconvert internally and spontaneously, i.e., shapeshift, between multiple chemical structures with varying pharmacophore properties. In one preferred embodiment, the invention include systems, methods, and compositions for the synthesis of novel bullvalene amino acid (Bvas) compounds that may further be incorporated into Shape Shifting Cyclic Peptides (SSCP) with varying pharmacophore properties and their use as novel therapeutic compounds.

4 Claims, 16 Drawing Sheets

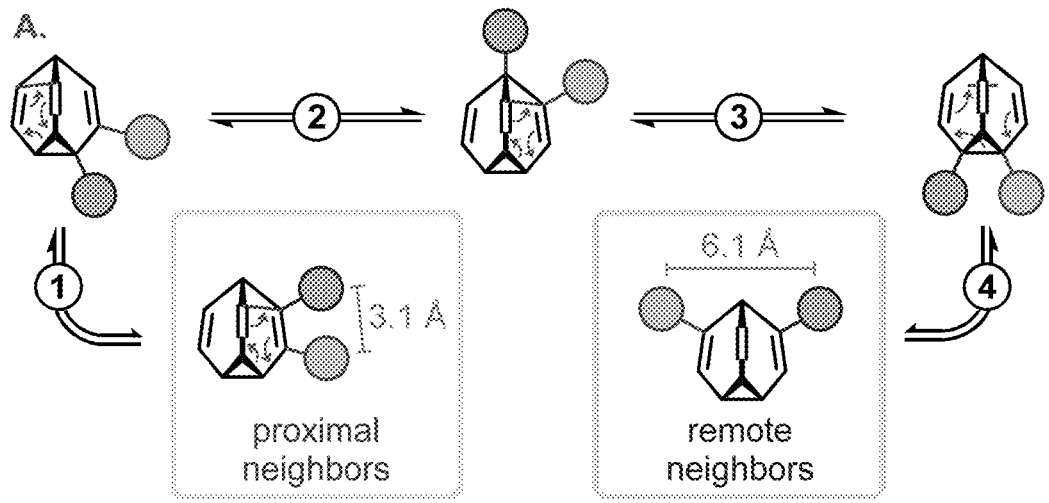
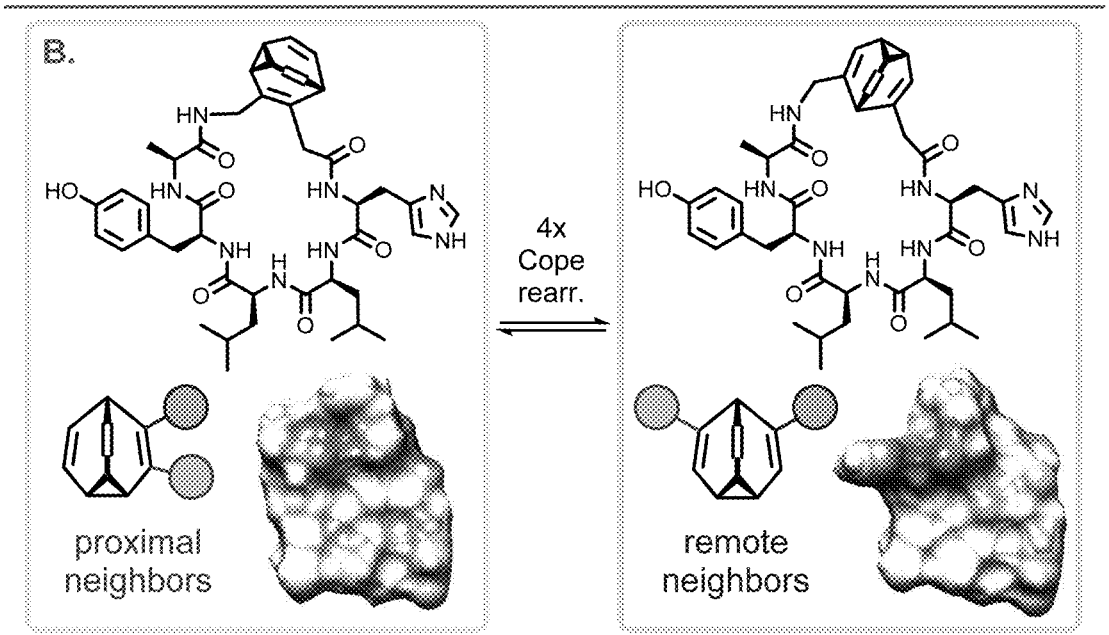
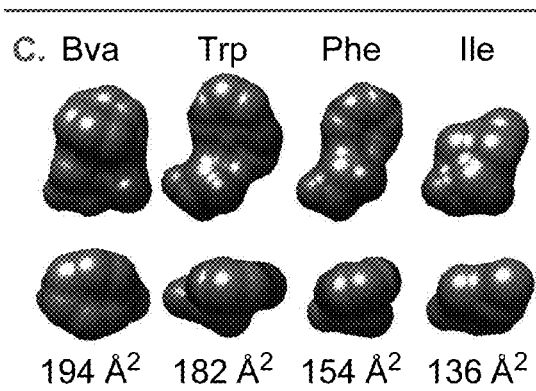
FIG. 1A-D

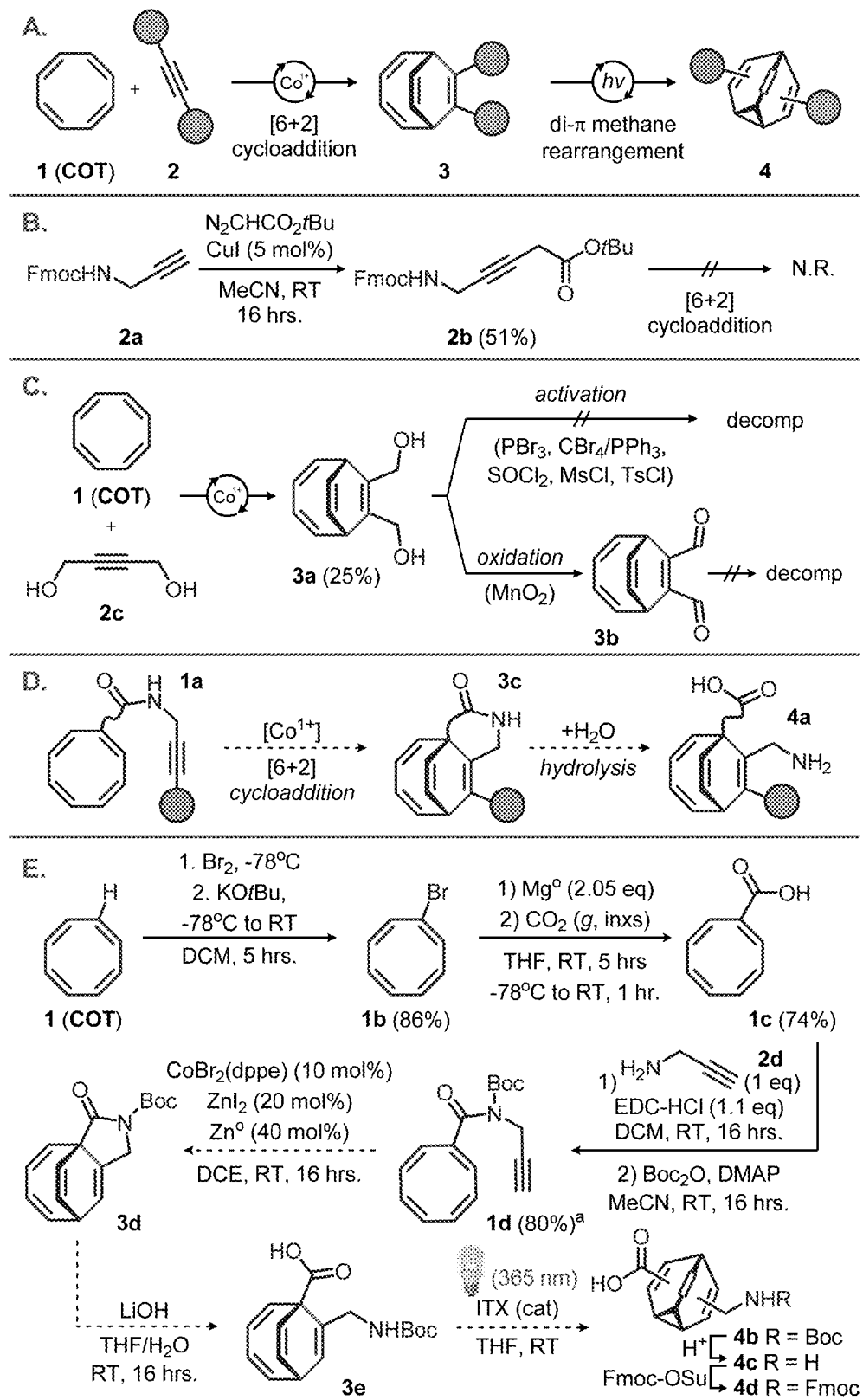
FIG. 2A-E

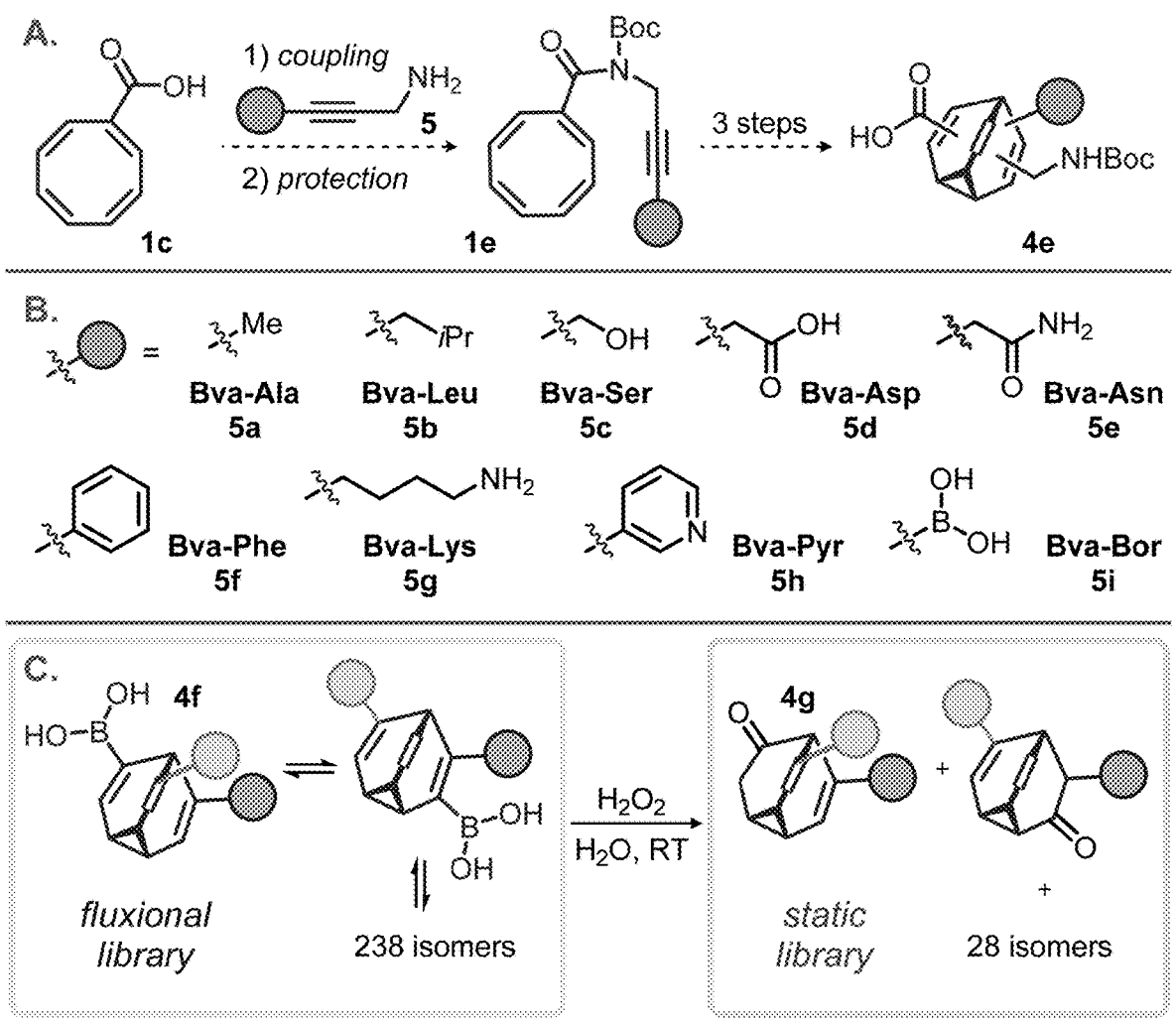
FIG. 3A-C

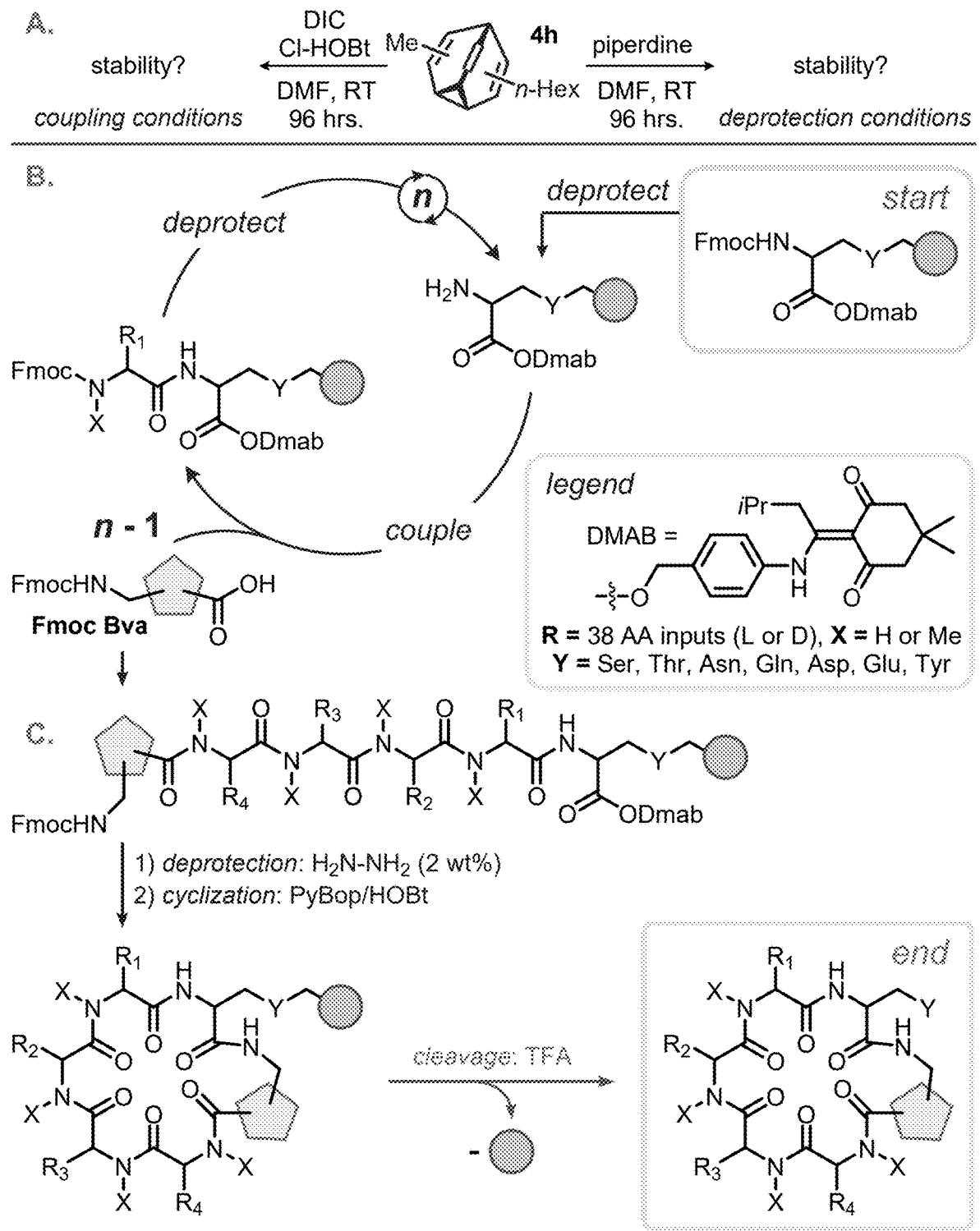
FIG. 4A-C

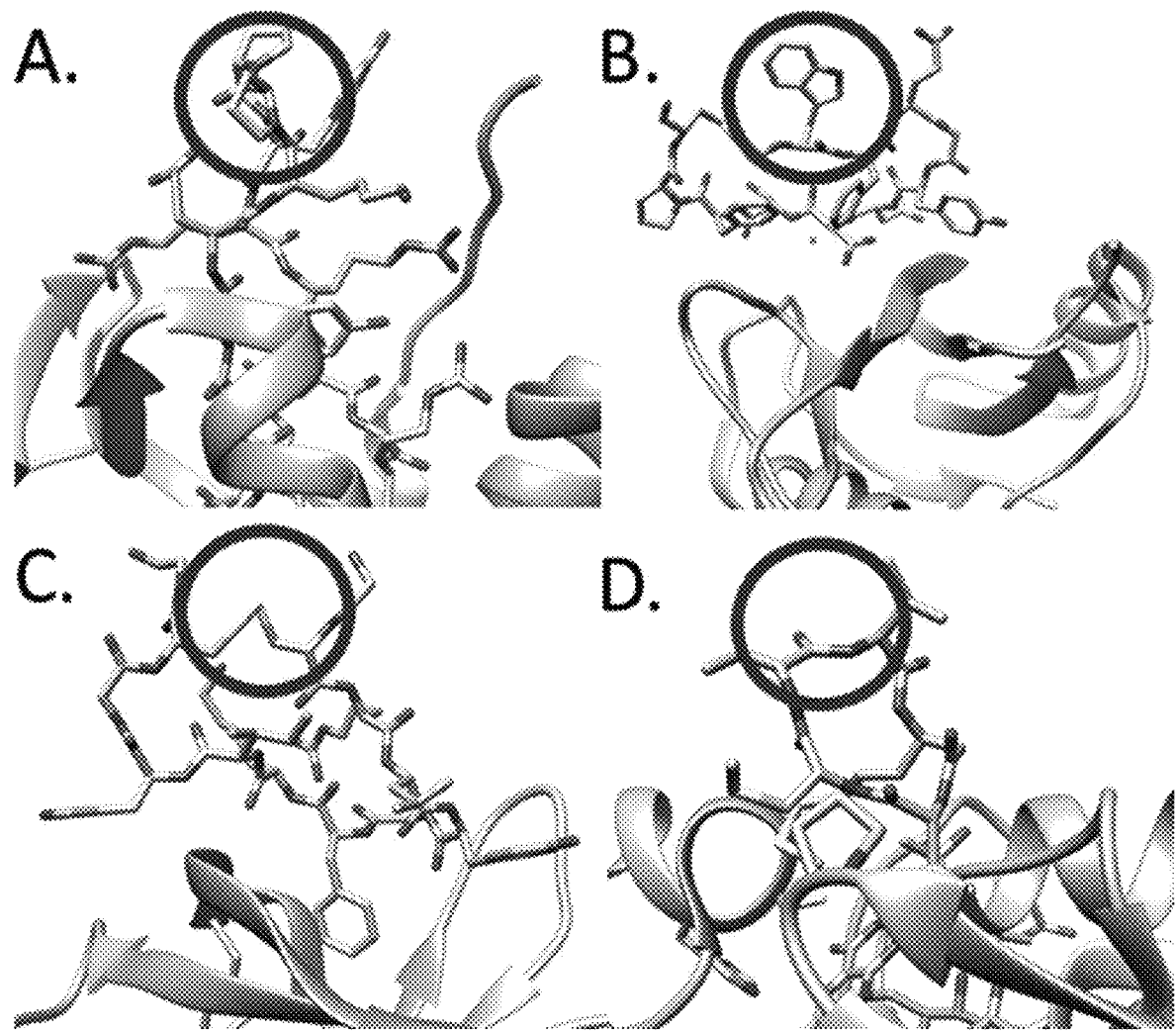
FIG. 5A-D

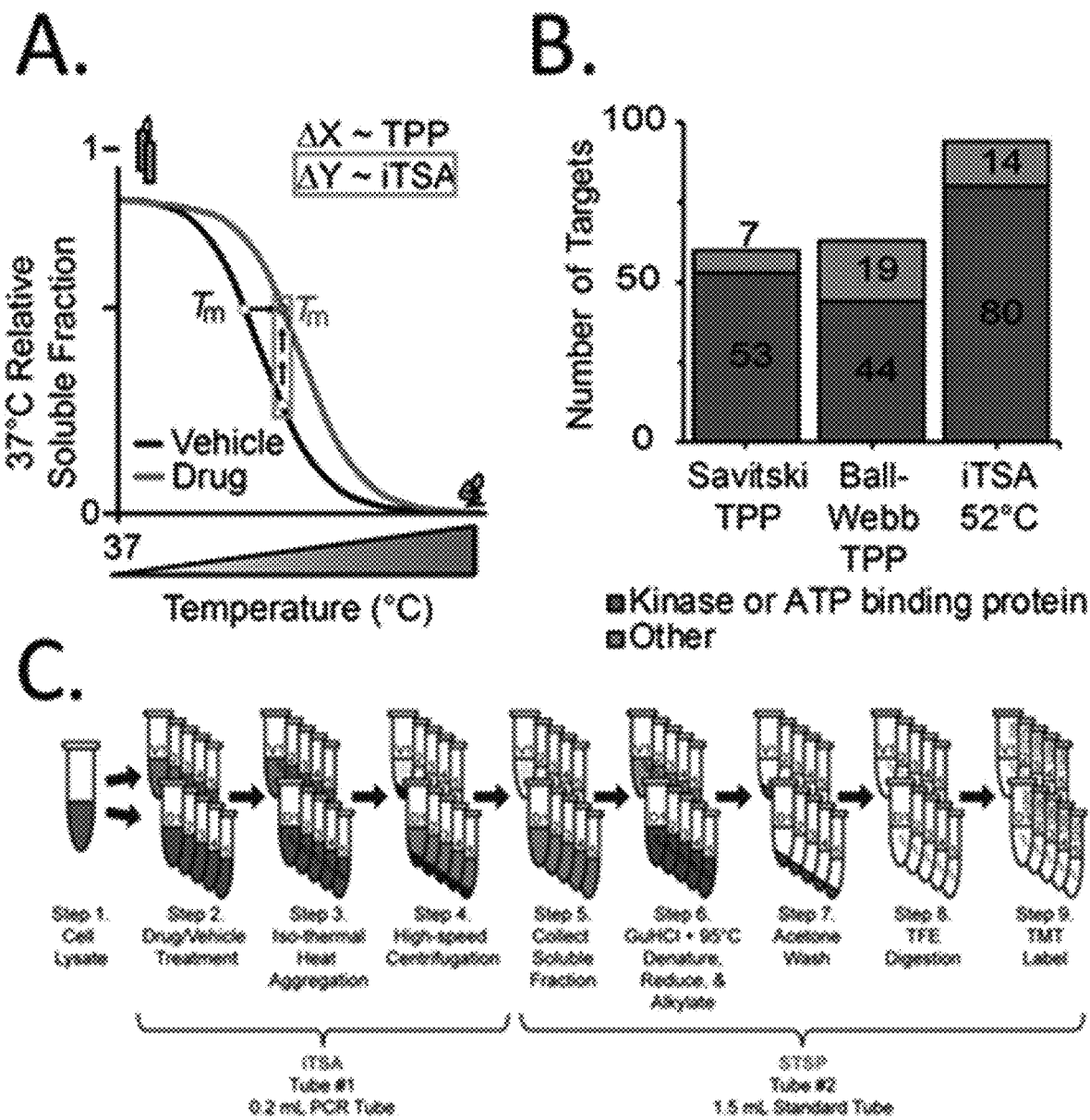
FIG. 6A-C $$N = \frac{20^{n-l-f}}{n}(n+b-1)(L \cdot n^l) \cdot 20^s \frac{10!}{3(10-c-s)!}$$

n = number of AAs in ring
f = number of bullvalenes on Class II ring
b = number of bullvalenes in Class IA or IB rings
l = number of linkers to resin
L = types of linking AAs to resin
c = number of Bullvalene links to ring
s = number of bullvalene functionalizations (excluding connections to ring)
Note: additional bullvalene structural isomer factors if b>1

Type IA: f = 0, c = 2, s = 0, b = 1
$$N = 20^{n-1}(L \cdot n)\frac{10!}{3(8!)}$$

Type IB: f = 0, c = 2, 8 > s > 0, b = 1
$$N = 20^{n-1}(L \cdot n) \cdot 20^s \frac{10!}{3(10-2-s)!}$$

Type II: n > f > 0, c = 1, 8 > s > 0, b = 0
$$N = 20^{n-2}(n-1) \cdot L \cdot 20^s \frac{10!}{3(10-1-s)!}$$

Type IC: f = 0, c = 2, 8 > s1 > 0; 8 > s2 > 0, b = 2
$$N = 20^{n-1} \cdot L(n+1)n \frac{20^{s1} \cdot 10!}{3(10-2-s1)!} \frac{20^{s2} \cdot 10!}{3(10-2-s2)!}$$

FIG. 12

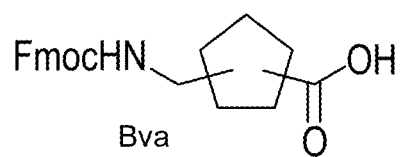
FIG. 21 (IV)
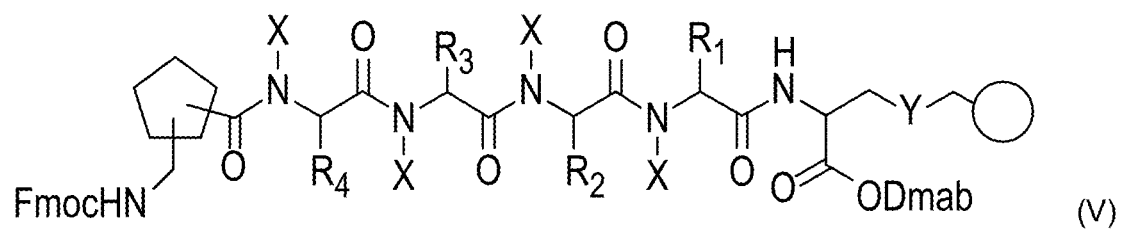
FIG. 22 (V)
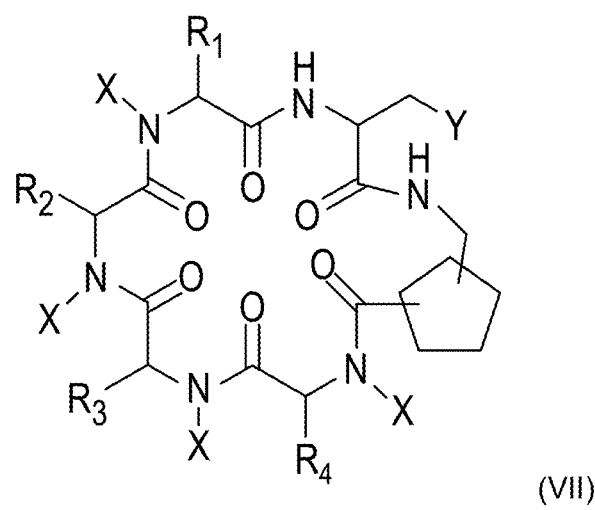
FIG. 23 (VII)

COMPOSITIONS AND METHODS OF SYNTHESIZING SHAPE SHIFTING CYCLIC PEPTIDES (Sscp) AND THEIR USE IN THE IDENTIFICATION OF NOVEL THERAPEUTIC COMPOUNDS

CROSS-REFERENCE TO RELATED APPLICATIONS

This application is a national stage application under 35 U.S.C. 371 of PCT Application No. PCT/US22/12880 having an international filing date of Jan. 19, 2022, which designated the United States, which PCT application claimed the benefit of U.S. Application Ser. No. 63/139,080, filed Jan. 19, 2021, both of which are incorporated by reference in their entirety.#

TECHNICAL FIELD

The invention described herein include systems, methods, and compositions for the synthesis of novel bullvalene amino acid (Bvas) compounds that may further be incorporated into Shape Shifting Cyclic Peptides (SSCP) with varying pharmacophore properties and their use as novel therapeutic compounds. The invention described herein is further directed to the field of peptide libraries and specifically in the area of fluxional peptide libraries of bullvalene containing peptides, and preferably SSCP, for design and selection of protein binding agents.

BACKGROUND

Despite decades of intensive effort to discover new therapeutic drugs, small molecules remain blunt instruments for manipulating human physiology. The chemical space of known drugs represents only a miniscule fraction of the $\sim 10^{63}$ possible drug-like molecules. Furthermore, the targets of these drugs represent only ~3.5% of the ~20,000 proteins in the human proteome leaving nearly 97% of the proteome untapped for drug intervention. These two factors combine to offer tremendous potential for discovering new chemical structures for treating disease. To overcome these limitation, the present inventive technology addresses this diversity enumeration barrier by creating an entirely new class of molecules that can spontaneously "shape shift" at room temperature and thereby adopt a diverse ensemble of rapidly interconverting structural isomers. In one embodiment, the invention proposes the development of an unnatural bullvalene amino acid that can be dragged-and-dropped into traditional methodologies for the combinatorial solid phase peptide synthesis to create Shape Shifting Cyclic Peptides (SSCP). One preferred embodiment, the invention described herein may include the creation of a physically viable fluxional library of SSCP with diversity that far exceeds that of any known library and will provide researchers with a novel pharmacological toolbox to tackle the grand challenge of drugging the undruggable.

SUMMARY OF THE INVENTION

One aspect of the current invention includes novel systems, methods, and compositions for the synthesis of novel shapeshifting bullvalene cyclic peptides and their use in the identification as novel therapeutic compounds, and in particular the production of known cyclic peptide drugs analogs containing bullvalene cyclic peptides.

Another aspect of the invention includes one or more novel bullvalene amino acid (Bvas) compositions or matter, and preferably one or novel more Fmoc bullvalene amino acids (Fmoc-Bvas) compositions or matter. In another preferred aspect, such Fmoc-Bvas may be incorporated into a Fmoc-solid phase peptide synthesis (SPPS) system forming a linear peptide coupled with a Fmoc-Bvas that may be cyclized forming a Shape Shifting Cyclic Peptide (SSCP). Additional aspects of the invention may include one or more Bva cyclic peptide analogs of known cyclic peptide drugs.

Another aspect of the current invention includes the development of a robust and scalable synthetic methods for producing Fmoc Bvas. In one preferred aspect, the invention includes systems, methods, and compositions for the use of intramolecular metal-catalyzed cycloaddition to forge key intermediates towards the synthesis of various Fmoc Bvas. In one preferred aspect, one or more bullvalene amino acids, such as Fmoc-Bva-Gly, may be synthesized which may further compromise specifically a bullvalene core substituted with a carboxylic acid and an Fmoc-protected amine (analogous to glycine).

Another aspect of the invention include the synthesis of tri-substituted bullvalene amino acids that have canonical and non-canonical side chains, further increasing the number of achievable fluxional isomers, chemical functionality, and reactivity. As shown below, the inventors demonstrate the preparation of at least 10 exemplary Fmoc Bva analogs with functional side chains that incorporate canonical polar and non-polar groups to provide chemical similarity to the parent peptide as described below. In one preferred aspect, the invention includes systems, methods, and compositions for the preparation of a boronic acid substituted Bva (Bva-Bor) that allows for an ensemble of structural isomers to be locked into their equilibrated states for characterization of poly-pharmacology described generally herein.

One aspect of the current invention includes a demonstration of the compatibility of Bva with solid phase peptide synthesis and synthesize Bva cyclic peptide analogs of known cyclic peptide drugs. In one preferred aspect, one or more representative Bva analogs and Fmoc Bvas may be produced and tested for stability under SPPS conditions using NMR and HPLC analytical methods. As most short cyclic peptides require less than 12 hours to synthesize using SPPS methods, the Bva analog may further be subjected to SPPS conditions, i.e., DIC, piperidine, DMF, etc., and monitored by NMR and HPLC over a period of at least 96 hours at room temperature and assessed for stability. This aspect may provide boundary conditions for SPPS stability tests using a short 4 mer Bva containing peptide. Subsequently, an exemplary Fmoc Bva-Gly may be incorporated into several known cyclic peptide drugs analogs where a high-resolution 3D structure of the peptide drug bound to its target is known. This may include the CXCR4 receptor, CK2a, Chymotrypsin, and GRB7. A Bva-Gly may further be incorporated at a position that is free from protein interactions based upon the known 3D structures of the cyclic peptide target complex. Each of these exemplary Bva substituted cyclic peptides may be analyzed for fluxionality as well as their ability to engage multiple targets besides the known target of the parent peptide.

Another aspect of the current invention includes a demonstration of the fluxional nature of the Bva cyclic peptides the use of cellular thermal shift assays to evaluate target engagement. The fluxional nature of the SSCPs produced by the methods described herein may be analyzed using a cooled preparative HPLC isolation method previously described for bullvalene analogs. Peptides purified at elevated (60° C.) temperature can be cooled to 4° C. and analyzed by HPLC to determine the fluxional distribution of isomers. Subsequently a single peak from the low temperature separation may be allowed to equilibrate at 37° C. and analyzed again by HPLC at 4° C. to examine the isomer redistribution properties. In another aspect, the invention may employ a drug target assay to test the expected polypharmacology together with the expected bone-fide target engagement. This assay may be used with the Bva inserted cyclic peptide as well as the non-fluxional parent cyclic peptide.

Another aspect of the invention may include a fluxional peptide library, and methods of creating the same. As used herein a "fluxional peptide library" describes a collection of a plurality of peptides having one or more bullvalene amino acids (Bva). In one preferred aspect, a fluxional peptide library may include a plurality of rationally designed peptides having one or more bullvalene amino acid (Bva), that may further be cyclized to form SSCP. As detailed below, the SSCP of the invention can be prepared from canonical and/or non-canonical amino acids, for example bullvalene amino acids (Bva), using solid-state peptide synthesis techniques and can be readily sequenced.

In another aspect, the invention may include the use of a fluxional peptide library to screen for therapeutic targets. Due to the fluxional distribution of the structures of the library each individual SSCP may encompass multiple isomeric configurations representing a plurality of pharmacophores. As a result, the fluxional peptide library may include exponentially more potential pharmacophores that a standard peptide library. This library of pharmacophore SSCP structures may be screened for affinity for a desired target, such as a protein, protein fragment, or protein active site. SSCP showing affinity for one or more targets may be deconvoluted to identify the active compounds structure, sequence or pharmacophore, or ensemble of features provided by multiple compounds, leading to activity which can be used to identify and generate a stable peptide analog, or plurality of therapeutic analogs that demonstrate specific activity towards the desired target. In this embodiment, a stable peptide analog may be a therapeutic peptide.

Another aspect of the invention may include a digital fluxional peptide library, and methods of creating the same. As used herein a "digital fluxional peptide library" describes a library of peptides having one or more bullvalene amino acids (Bva) generated in silico, by a computer system having a process configured to execute an application designed to rationally design a plurality of peptides having one or more bullvalene amino acids (Bva), and further configured to calculate and produce in a virtual environment the three-dimensional structure, and fluxional distribution of any one member of the library. In one preferred aspect, a digital fluxional peptide library may include a plurality of rationally designed digital peptides having one or more bullvalene amino acid (Bva), that may be digitally cyclized to form SSCP. The system may reproduce in a virtual environment the three-dimensional structure, and fluxional distribution of any one SSCP member of the library.

In another aspect, the invention may include the use of a digital fluxional peptide library to screen for therapeutic targets. Due to the fluxional distribution of the digital structures of the library each individual SSCP may reproduce, in silico, multiple isomeric configurations representing a plurality of pharmacophores. As a result, the digital fluxional peptide library may include exponentially more potential pharmacophores that a standard peptide library. This digital library of pharmacophore SSCP structures may be screened in silico for affinity for a desired target, such as a protein, protein fragment, or protein active site that may also be rendered in silico. SSCP showing affinity for one or more targets may be deconvoluted in silico, to identify the active compound's structure, sequence or pharmacophore, or ensemble of features provided by multiple compounds, which can be used to identify and generate, in vitro or in silico, a stable peptide analog, or plurality of stable therapeutic analog s that demonstrate specific activity towards the desired target.

Additional aspects of the invention include a fluxional peptide library, which may preferably be populated with SSCP structures, which may optionally be digital to screen for enhanced peptide characteristics, such as cell permeability and stability, as well as specific affinity for one or more targets.

Additional aspect of the various embodiments of the systems, methods, and compositions for the synthesis of SSCP will become readily apparent and better understood in view of the description and accompanying drawings.

BRIEF DESCRIPTION OF FIGURES

FIG. 1: (A) Proximal neighbors (3.1 Å) on a disubstituted bullvalene are separated to remote neighbors (6.1 Å) within 4 Cope rearrangements that occur at room temperature. (B) Left: an initial proximal neighbors' substitution of bullvalene in a cyclic peptide with its corresponding calculated 3D structure and Coulombic surface; right: a final remote neighbors isomer of bullvalene in a cyclic peptide with its corresponding calculated 3D structure and Coulombic surface. Note the dramatic difference in shape and electrostatic surface between proximal (left) and remote (right). (C) Surface area comparison of the proposed Bva and canonical amino acids. (D) Formula for calculating isomers of substituted Bva wherein a physical peptide library of $10^{11}$ peptides would contain $10^{11}*1680$ or $1.7*10^{14}$ total constitutional isomers, i.e., different pharmacaphores.

FIG. 2: (A) Fallon's 2-step synthesis of mono- and di-substituted bullvalenes. (B) Unsuccessful cycloaddition of COT with an amino acid internal alkyne. (C) Successful formation of a tetraene diol 3a and unsuccessful subsequent elaboration. (D) Proposed use of an intramolecular amide tether to increase efficacy of the Co(I)-catalyzed cycloaddition with internal alkynes. (E) The proposed synthetic route to bullvalene amino acids through intramolecular reactions.

FIG. 3: (A) Use of internal propargyl amines (5) to create tri-substituted bullvalenes. (B) Potential canonical and non-canonical side chains to be explored on bullvalene. (C) Conversion of a fluxional bullvalene library to a static library by oxidation of an ensemble of $sp^2$-hybridized boronic acids to ketones with aqueous $H_2O_2$.

FIG. 4: (A) Stability of a representative bullvalene under SPPS conditions. Generalized SPPS scheme for 6 membered cyclic peptide synthesis. (B) SPPS scheme. (C) On-resin cyclization and subsequent cleavage. $R_1$-$R_5$ includes over 160 natural and unnatural commercially available amino acids.

FIG. 5: Cyclic peptide drugs that will be synthesized with targeted Bva insertions at non interacting positions (blue circles). (A) CVX15 cyclic peptide bound to the CXCR4 receptor. (PDB 3OE0). (B) Cyclic peptide agonist bound to GRB7 (PDB 3PQZ). (C) CK2a bound to competitive cyclic peptide (PDB 4IB5). (D) Chymotrypsin bound to cyclic peptide inhibitor 5B (PDB 4Q2K).

FIG. 6: (A) Experimental principle of the iTSA experiment where a single temperature is used to identify stabilized proteins in the presence of a drug or metabolite. (B) Superior target identification observed using the iTSA method as compared to the traditional TPP method. (C) Workflow of the iTSA MS method developed by the present inventors.

FIG. 12: Identification of Bullvalene isomer counts.

FIG. 21: Shows a Fmoc bullvalene amino acid according to Formula (IV).

FIG. 22: Shows a Fmoc bullvalene containing peptide may include a linear peptide, such as a 4-mer, 6-mer, 8-mer or 10-mer or larger, according to generalized Formula (V).

FIG. 23: Shows a cyclic peptide may include a shape shifting cyclic peptide (SSCP) containing at least one bullvalene structure according to Formula (VII).

DETAILED DESCRIPTION OF THE INVENTION

Figure 7:
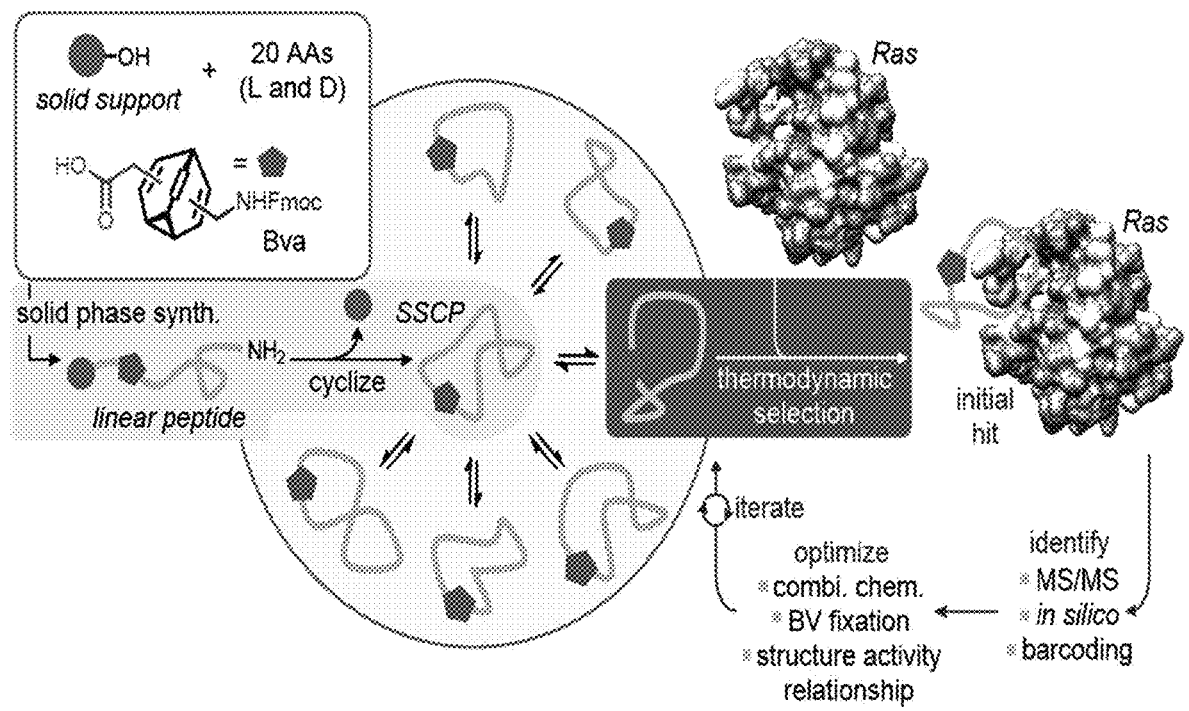
FIG. 7: Diagram of the inventive platform for the development of Shape Shifting Cyclic Peptides (SSCP). As shown, the diagram shows the work-flow for preparing cyclic peptides (CPs) that can sample various topologies, shapes, and functions in vitro and in vivo combined with rapid thermal profiling technology recently developed.
Figure 8:
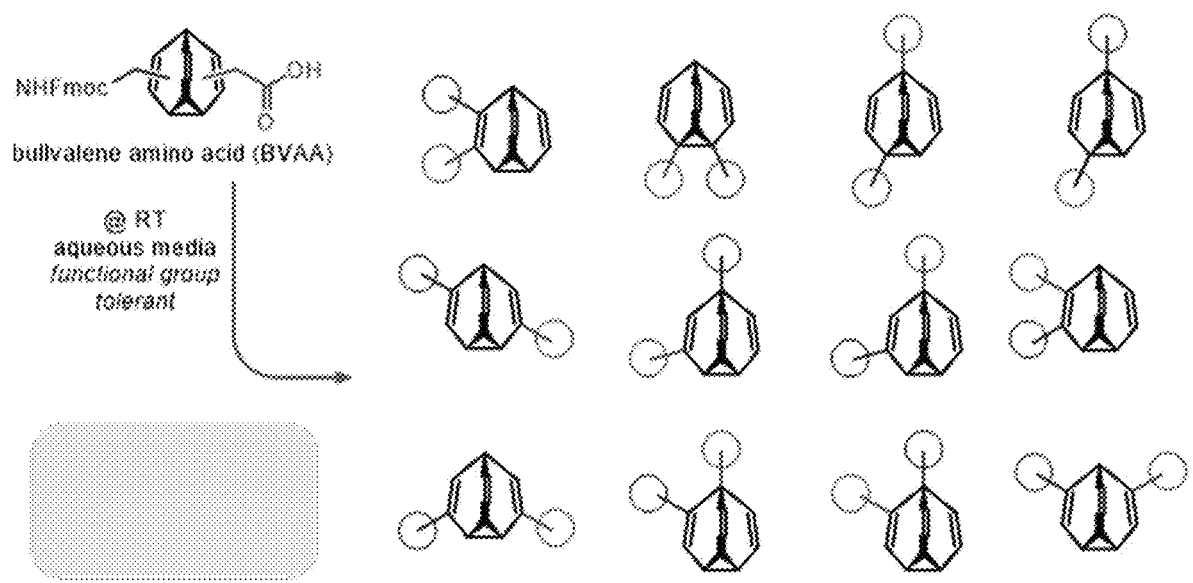
FIG. 8: Internalized library from bullvalene showing various equilibrating structural isomers.
Figure 9:
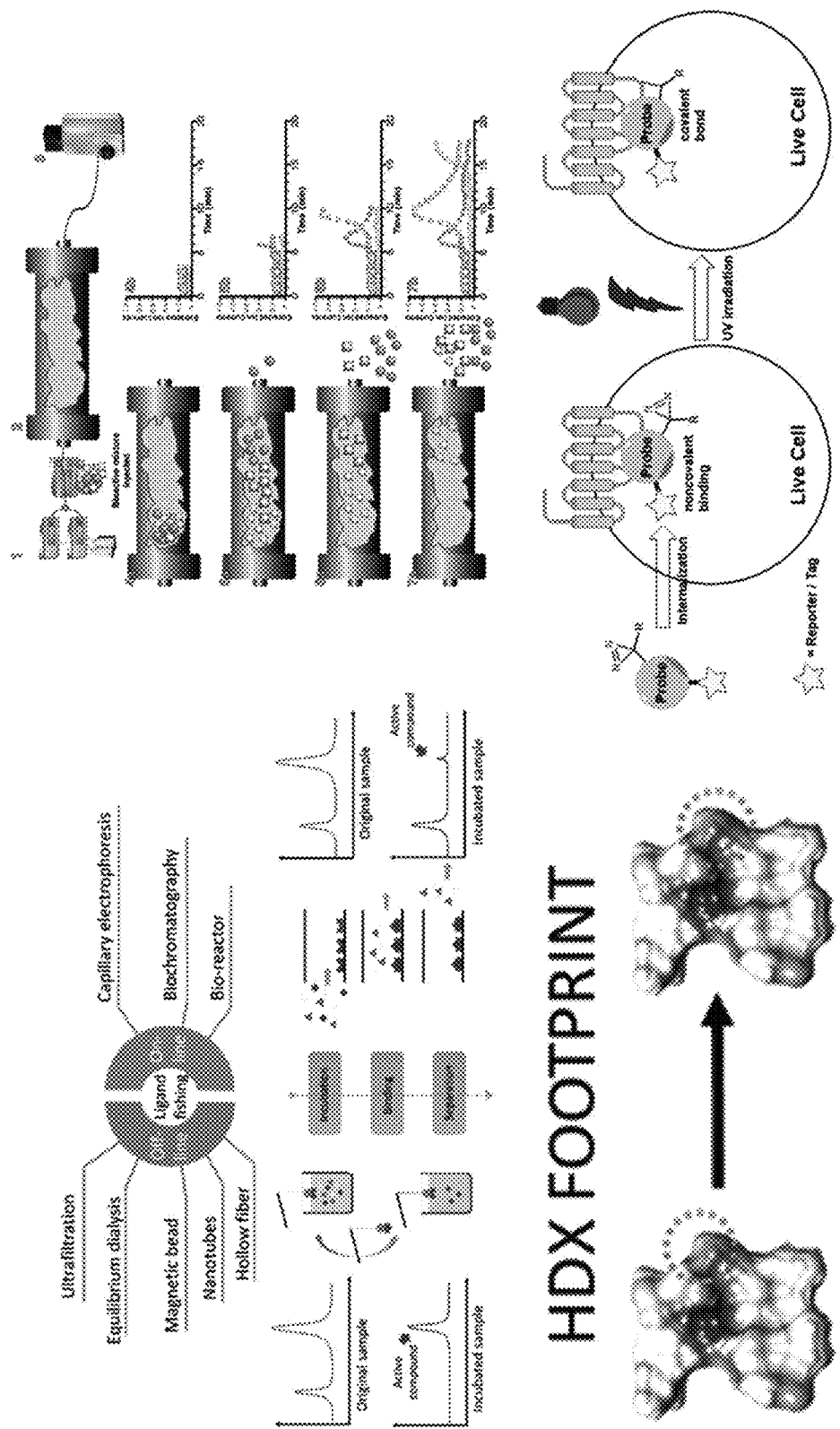
FIG. 9: Shows multiple schematic diagrams of independent approaches to identify SSCP hits including: Mass-barcoding for gas-phase sequencing and ID of tight-binders; Custom affinity-selection LC/MS to ID slow $k_{off}$ binders; and HDX-LC/MS to ID binders and buried backbone amides.
Figure 10:
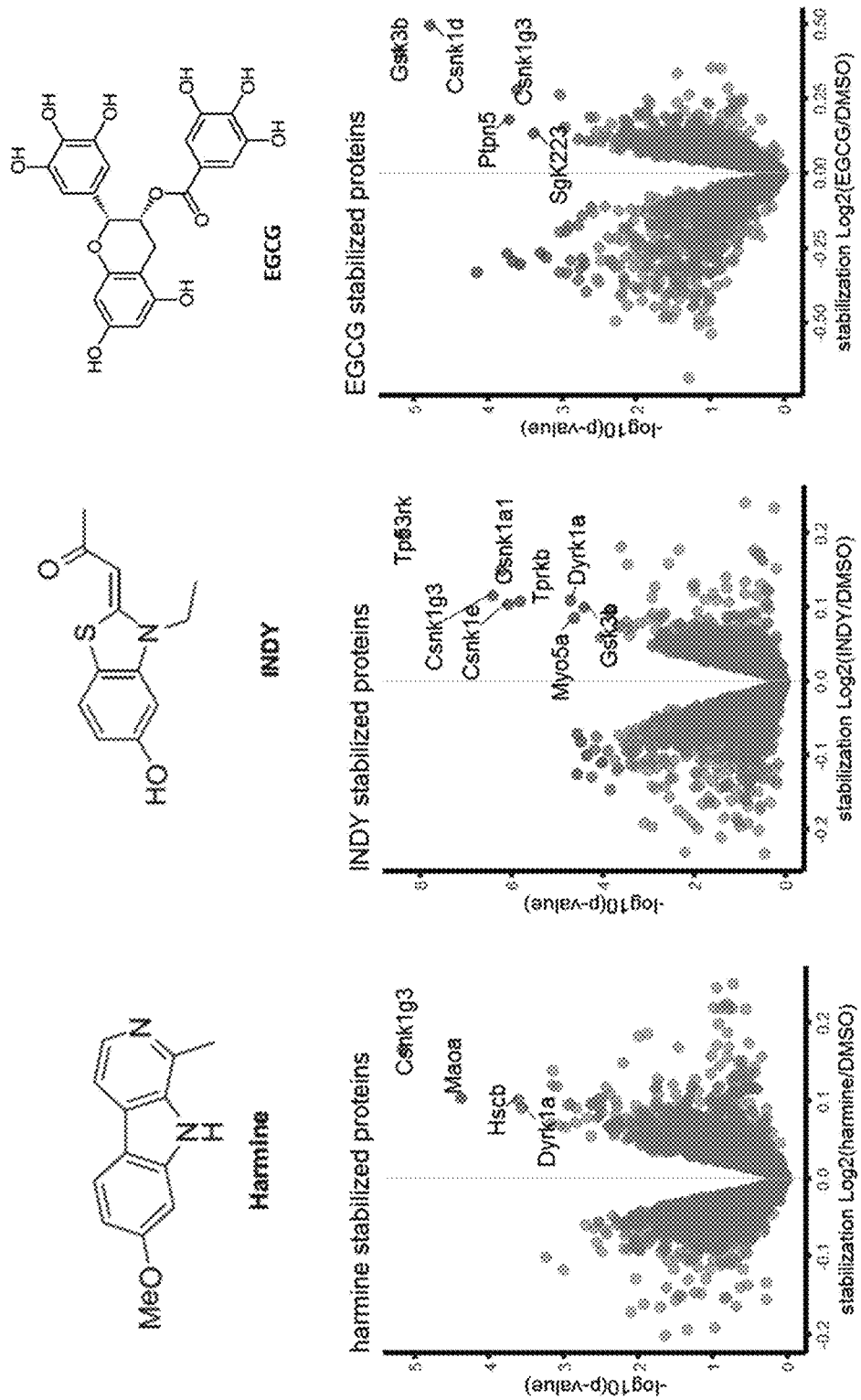
FIG. 10: Isothermal Shift Assay example demonstrating identification of SSCP binding and off-target hits
Figure 11:
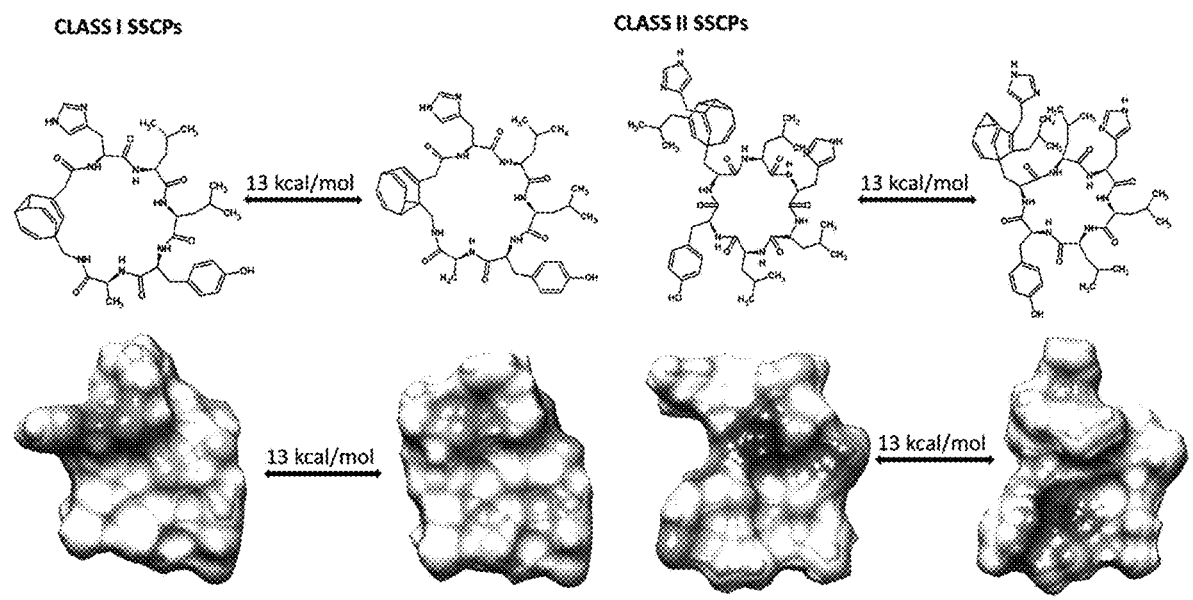
FIG. 11: Exemplary Class I and Class II SSCP variants.

As noted above, the driving rational for developing such shapeshifting peptides arises from the practical upper limits imposed on synthetic methods for the creation of structural diverse molecules and number of molecules that can be practically screened, particularly in the context of traditional diversity-oriented screening. To overcome the inherent limits of diversity and scale for targeting the human proteome, the present inventors proposed herein the development of novel shape-shifting amino acids and linkers, creating structurally dynamic libraries comprising greater than $10^{14}$ constitutionally distinct structural species. This may be achieved through the synthesis of novel bullvalene amino acid derivatives suitable for large scale and efficient combinatorial solid phase peptide synthesis (SPPS).

As shown in FIG. 1A, the molecule responsible for the creation of these structurally diverse species is nicknamed "bullvalene", which is a compact, rigid molecule containing three ethylene bridges and a cyclopropane capable of undergoing rapid [3,3]-sigmatropic Cope rearrangements at room temperature. The exhaustive Cope rearrangements within bullvalene break and reform carbon bonds, allowing for substituents to roam around the core, much like a molecular ball joint. Because these rearrangements are intramolecular and spontaneous, they do not suffer from loss in fidelity and do not require an exogenous catalyst, issues that plague and complicate other common dynamic chemistries. Furthermore, the molecular diversity developed by bullvalene has been rigorously explored and is fully internalized within a singular molecule, requiring no additional coupling partners to introduce structural variety. Indeed, un-functionalized bullvalene can have up to 1,209,600 stable constitutional isomers that constantly interconvert at room temperature.

As further demonstrated in FIG. 1B, the incorporation of a bullvalene amino acid (Bva) into cyclic peptides creates a dynamic library of poly-pharmacophores for efficient targeting of undruggable targets in the human proteome. As also shown in FIGS. 1C-D, the relative surface area of Bva is comparable to that of aromatic amino acids and bullvalene isomers have been isolated chromatographically to give a single structural isomer stable at reduced temperatures, such that this discrete isomer, when heated to room temperature, may be shown to redistribute back to the complete family of interconverting structural bullvalene isomers it was isolated from, giving the theoretically expected isomer number.

As shown below, the present inventors demonstrate a novel strategy to exploit the fluxional nature of bullvalene to achieve previously unobtainable library sizes of synthetic cyclic peptides with inherent poly-pharmacology. The incorporation of bullvalene into cyclic peptides generates internalized diversity within singular molecules, spontaneously sampling various tertiary structures and electrostatic surfaces, thus, creating molecular diversity that could not previously be created by any other known chemical methods.

Figure 13:
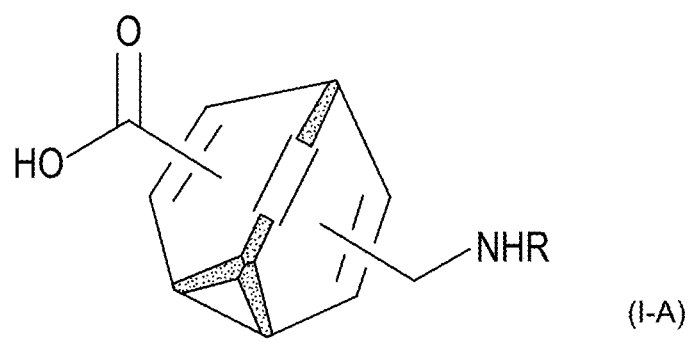
FIG. 13: Shows the compound according to Formula I-A.

The invention may include one or more compositions comprising an amino acid compound containing a bullvalene structure. In one preferred embodiment, the invention may include a di-substituted bullvalene amino acid (Bva) according to Formula (I-A) as shown in FIG. 13:

In this embodiment, R may be an H, or a protecting group such as a Boc, or Fmoc. In embodiments wherein R is Fmoc, the invention may include an Fmoc bullvalene amino acid (Fmoc Bva) as generally described herein.

Figure 14:
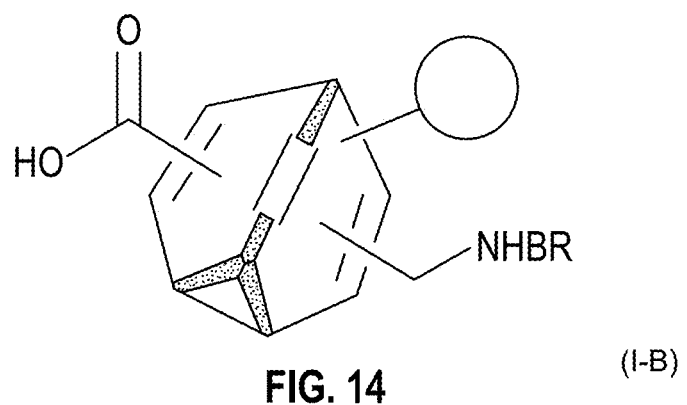
FIG. 14A: Shows the compound according to Formula I-B.

In another preferred embodiment, the invention may include a tri-substituted bullvalene amino acid (Bva) according to Formula (I-B) as shown in FIG. 14.

Figure 15:
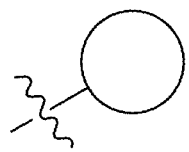
FIG. 15: Represents the symbol for a variably position along the bullvalene structure.

In this embodiment, the symbol shown in FIG. 15 may be variably position along the bullvalene structure and may further comprise a canonical and/or non-canonical side-chain such as a canonical and/or non-canonical amino acid. In one preferred embodiment, the symbol shown in FIG. 15 may be optionally selected from the group consisting of:

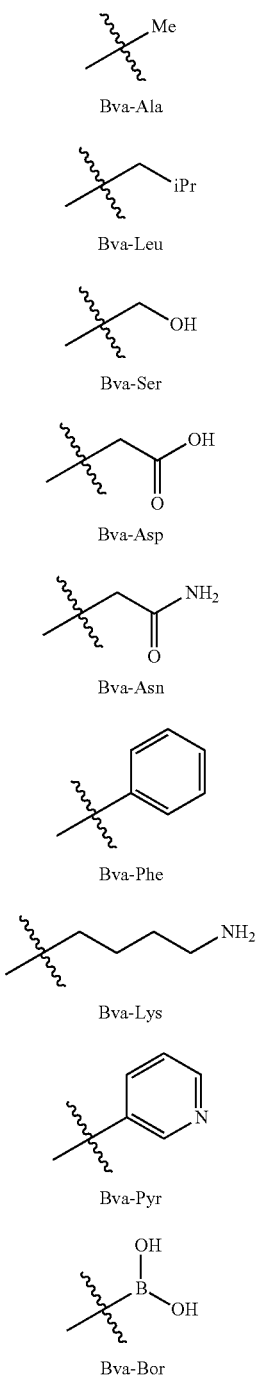

In the embodiment shown above, R may be an H, or a protecting group such as a Boc, or Fmoc. In embodiments wherein R is Fmoc, the invention may also be generally referred to as an Fmoc bullvalene amino acid (Fmoc-Bva).

Figure 16:
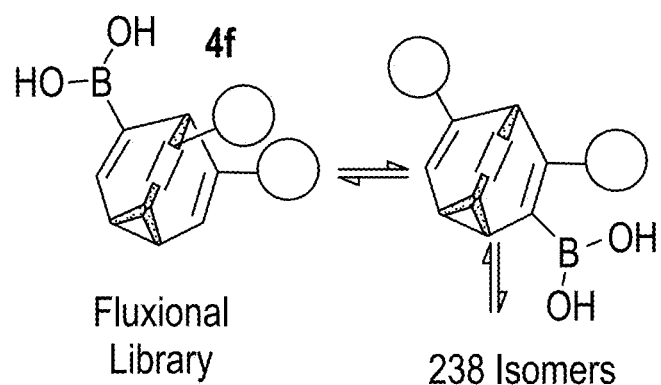
FIG. 16: Shows an amino acid compound containing a fluxional boronic acid according to Formula (I-C).

The invention may include one or more compositions comprising an amino acid compound containing a fluxional boronic acid according to Formula (I-C). As shown below, compound according to Formula (I-C) is fluxional, such that the side-chain may form a bullvalene library of compound comprising at least 238 isomeric configurations as shown in FIG. 16.

Figure 17:
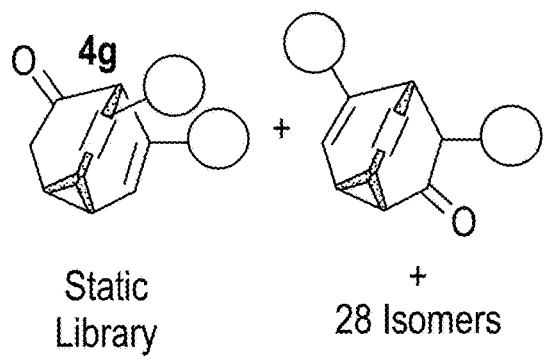
FIG. 17: Shows a compound containing a static bullvalene library composition according to Formula (I-D).

The invention may include one or more compositions comprising a compound containing a static bullvalene library composition according to Formula (I-D). As shown below, compound according to Formula (I-D) is static, such that the side-chain may form a bullvalene library of compound comprising at least 28 isomeric configurations as shown in FIG. 17.

As note below, a bullvalene containing compounds, and preferably an Fmoc-Bva may be incorporated into a Fmoc-solid phase peptide synthesis (SPPS) system forming a linear peptide coupled with said Fmoc-Bva which may further be cyclized forming a Shape Shifting Cyclic Peptide (SSCP). This process may be employed as generally described herein to produce a plurality of SSCP's forming a library of SSCPs that may have activity towards one or more targets, and/or have one or more therapeutic activities, preferably in a human. In one preferred embodiment, one or more SSCP analogs of cyclic peptide drugs may be generated as part of a library and further tested for target activity or therapeutic effect.

The invention further includes methods of synthesizing one or more bullvalene containing compounds, and preferably methods of synthesizing a hetero-disubstituted bullvalene amino acid (Bva). In one preferred embodiment, a cyclooctatetraene (COT) is mono-brominated to form compound 1b which is then converted to a Grignard reagent and reacted with $CO_2$ to from the acid compound 1c,

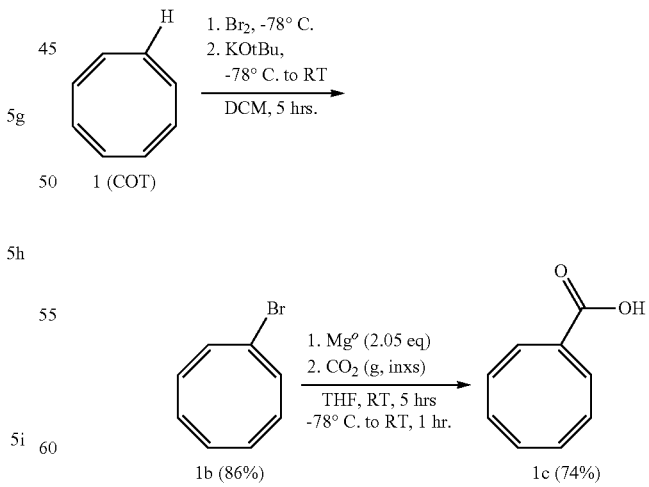

Next, compound 1c may reacted with a propargyl amine 2d in the presence of boc anhydride ($Boc_2O$) producing decorated COT compound 1d, or alternatively direct activation of amide of 1d with Fmoc-Osu may be accomplished.

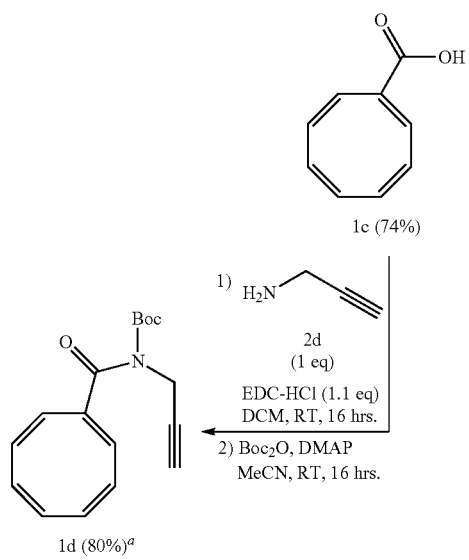

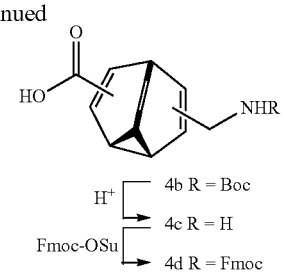

Compound 4b next undergoes deprotection of the Boc-group with an acid to produce compound 4c, followed by reaction with N-(9-fluorenylmethoxycarbonyloxy)succinimide (Fmoc-OSu) under basic conditions producing the Fmoc-Bva of compound 4d which include an Fmoc-Bva compound as generally described herein.

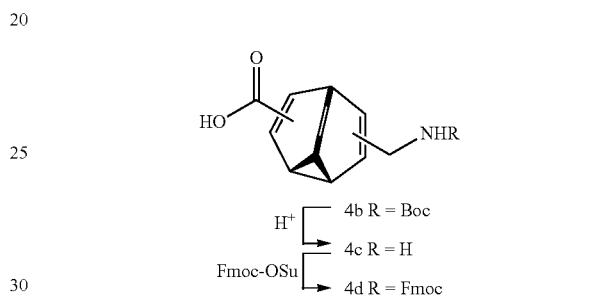

Compound 1d may undergo intramolecular Co(I)-catalyzed cycloaddition to produce compound 3d which further undergoes hydrolysis of the Boc-appended amide to furnish compound 3e in this embodiment.

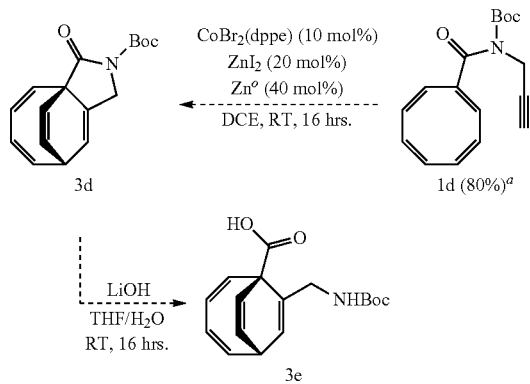 [SMILES: CC(C)(C)OC(=O)N1CC2=C[C@H]3C=C[C@@]2(/C=C\C=C/3)C1=O ; C#CCN(C(=O)OC(C)(C)C)C(=O)C1=C/C=C\C=C/C=C\1 ; "LiOH" ; CC(C)(C)OC(=O)NCC1=C[C@H]2C=C[C@]1(C(=O)O)/C=C\C=C/2]

Next, Compound 3e may undergoe photo-induced di-π methane rearrangement in the presence of catalytic quantities of a triplet sensitizer (ITX) to form the fluxional boc-protected bullvalene amino acid of compound 4b.

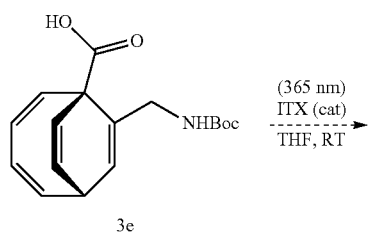

Figure 18:
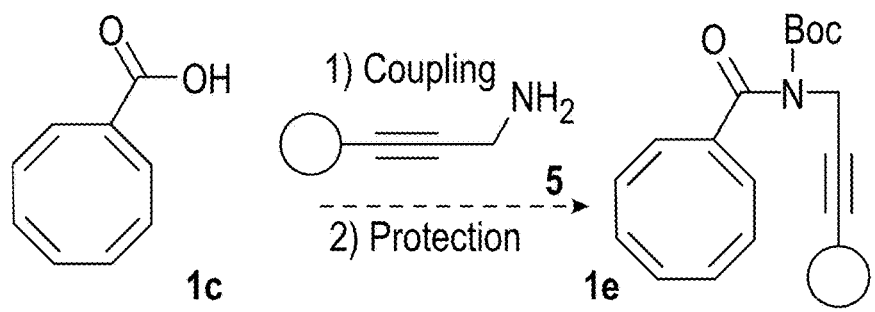
FIG. 18: Shows a facile amide coupling of compound 1c with propargyl amine of compound 5 is accomplished, followed by reaction with Boc$_2$O to produce tethered COT core compound 1e.

The invention further includes methods of synthesizing one or more bullvalene containing compounds, and preferably methods of synthesizing a tri-functional bullvalene amino acid (Bva). In this preferred embodiment, a cyclooctatetraene (COT) is mono-brominated to form compound 1b which is then converted to a Grignard reagent and reacted with $CO_2$ to from the acid compound 1c as described above. Next, facile amide coupling of compound 1c with propargyl amine of compound 5 is accomplished, followed by reaction with $Boc_2O$ to produce tethered COT core compound 1e as shown in FIG. 18.

Figure 19:
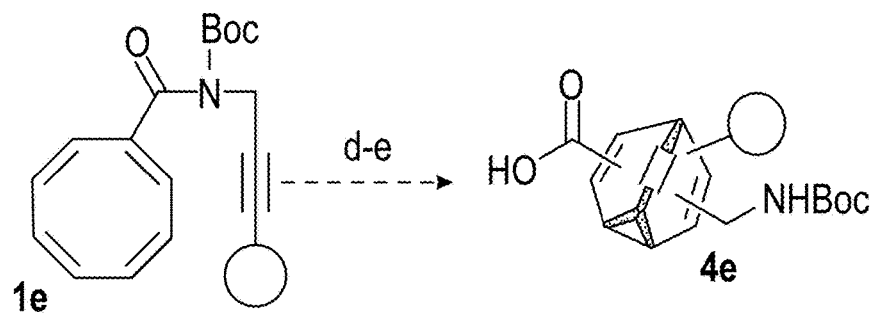
FIG. 19: Shows a compound undergoing photo-induced di-π methane rearrangement in the presence of catalytic quantities of a triplet sensitizer (ITX) to form the fluxional boc-protected bullvalene amino acid of compound 4e.

Next, as generally described above, compound 1e undergoes intramolecular Co(I)-catalyzed cycloaddition which further undergoes hydrolysis of the Boc-appended amide. The resulting compound undergoes photo-induced di-π methane rearrangement in the presence of catalytic quantities of a triplet sensitizer (ITX) to form the fluxional boc-protected bullvalene amino acid of compound 4e as shown in FIG. 19.

In an optional embodiment, compound 4e may undergo deprotection of the Boc-group with an acid followed by reaction with N-(9-fluorenylmethoxycarbonyloxy)succinimide (Fmoc-OSu) under basic conditions producing a fluxional Fmoc-Bva as generally described herein.

In this embodiment, the symbol shown in FIG. 15 may be variably position along the bullvalene structure and may further comprise a canonical and/or non-canonical sidechain such as a canonical and/or non-canonical amino acid. In one preferred embodiment, the symbol shown in FIG. 15 may be optionally selected from the group consisting of:

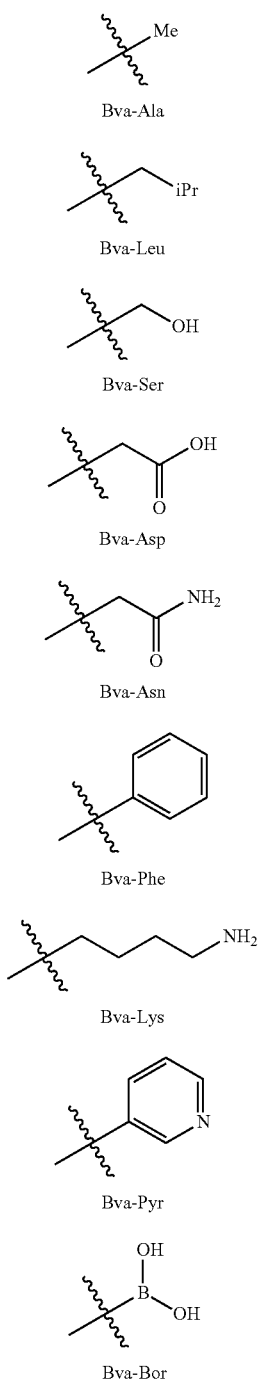

5a Bva-Ala
5b Bva-Leu
5c Bva-Ser
5d Bva-Asp
5e Bva-Asn
5f Bva-Phe
5g Bva-Lys
5h Bva-Pyr
5i Bva-Bor

Figure 20:
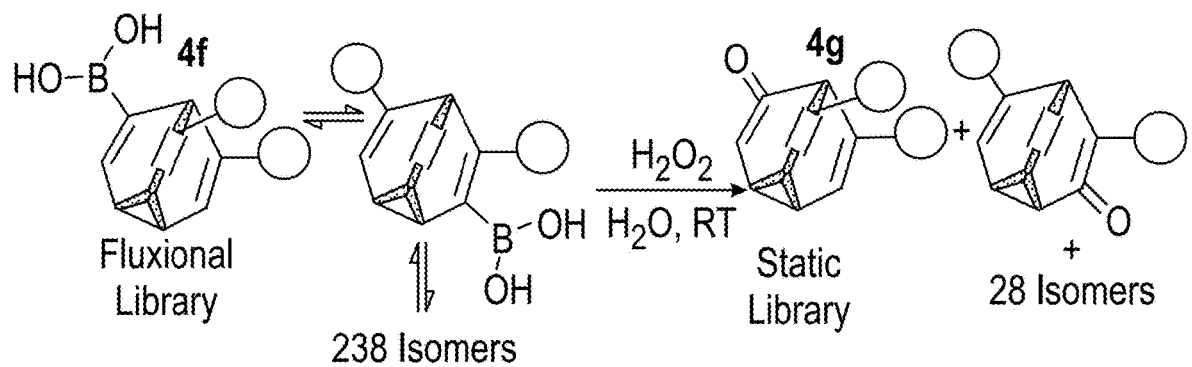
FIG. 20: Shows a fluxional Bva-Bor compound 4f is reacted with excess hydrogen peroxide (H$_2$O$_2$), which oxidizes the boronic acid to an enone that tautomerizes to a ketone forming the static bullvalone of compound 4g having 28 isomer combinations.

In invention further includes methods of generating a static bullvalene containing compounds, and preferably a tri-substituted boronic acid containing bullvalene (Bva-Bor) in a locked configuration. As shown below, in this embodiment, a fluxional Bva-Bor compound 4f is reacted with excess hydrogen peroxide ($H_2O_2$), which oxidizes the boronic acid to an enone that tautomerizes to a ketone forming the static bullvalone of compound 4g having 28 isomer combinations as shown in FIG. 20.

The invention includes additional compositions including one or more canonical or non-canonical amino acids having a bullvalene, and in some preferred embodiments a protecting group, such as an Fmoc to facilitate further chemistries as described below. In one preferred embodiment of the invention, a peptide may include at least one Fmoc bullvalene amino acid according to Formula (IV) as shown in FIG. 21.

In alternative embodiment, Fmoc bullvalene containing peptide may include a linear peptide, such as a 4-mer, 6-mer, 8-mer or 10-mer or larger, according to generalized Formula (V) as shown in FIG. 22:

wherein:
X is H or Me;
$R_1$-$R_4$ is an L or D amino acid, wherein said amino acid is a canonical amino acid or a non-canonical amino acid;
Y is an amino acid, and preferably an amino acid selected from the group consisting of: Ser, Thr, Asn, Gln, Asp, Glu, and Tyr; and
Dmab is:

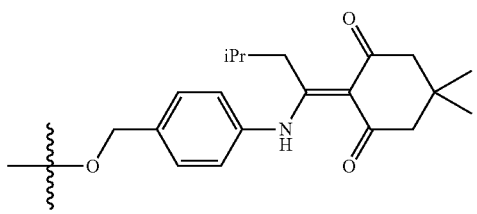 [SMILES: *OCc1ccc(NC(CC(C)C)=C2C(=O)CC(C)(C)CC2=O)cc1]

The invention may further include one or more cyclic peptides containing at least one Fmoc bullvalene amino acid according to Formula (IV) as shown in FIG. 21:

In this embodiment, the cyclic peptide may include a shape shifting cyclic peptide (SSCP) containing at least one bullvalene structure according to Formula (VII) as shown in FIG. 23:

wherein:
X is H or Me;
$R_1$-$R_4$ is an L or D amino acid, wherein said amino acid is a canonical amino acid or a non-canonical amino acid; and
Y is an amino acid, and preferably an amino acid selected from the group consisting of: Ser, Thr, Asn, Gln, Asp, Glu, and Tyr.

As noted above, due to the fluxional nature of the bullvalene structure, such SSCPs may be formed to be analogs of known therapeutic cyclic peptide drugs. For example, such SSCPs may be generated that are analogs of cyclic peptide drugs directed to one or more targets, such as the CXCR4 receptor, GRB7, CK2a, or Chymotrypsin.

The invention further includes methods of determining the stability of a bullvalene amino acid core. In this preferred embodiment, a bullvalene amino acid (Bva) having the formula 4h is introduced to unitary Fmoc-solid phase peptide synthesis (SPPS) conditions of activation/coupling further comprising:

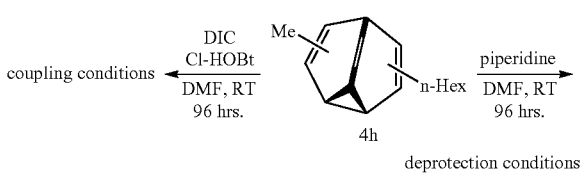

Figure 25:
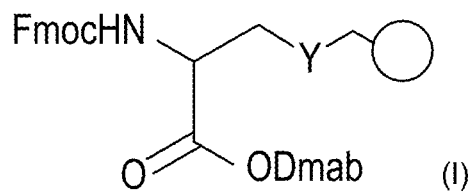
FIG. 25: A resin bound amino acid having a formula according to Formula (I) that can be used to synthesize a Shape Shifting Cyclic Peptides (SSCP) containing bullvalene amino acids.

The invention further includes methods of synthesizing Shape Shifting Cyclic Peptides (SSCP) containing bullvalene amino acids. In one preferred embodiment, a resin bound amino acid having a formula according to Formula (I) as shown in FIG. 25 may be established:
wherein:
Y is an amino acid, and preferably an amino acid selected from the group consisting of: Ser, Thr, Asn, Gln, Asp, Glu, and Tyr; and The invention includes a method of synthesizing peptide containing a bullvalene amino acid. In this embodiment, a Fmoc bullvalene containing peptide having a Fmoc-Bva according to Formula (IV) may be generated as described above, wherein the Fmoc bullvalene containing peptide comprises a compound according to Formula (V) according to FIG. 22:

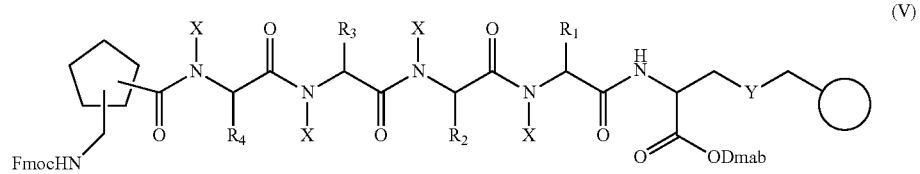

Dmab is:

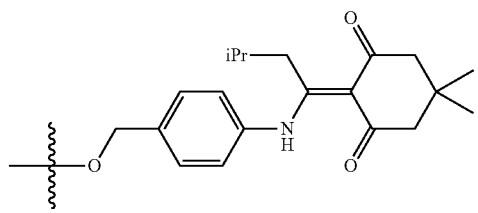 [SMILES: *OCc1ccc(NC(CC(C)C)=C2C(=O)CC(C)(C)CC2=O)cc1]

Figure 26:
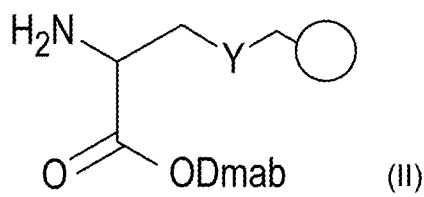
FIG. 26: Shows the chemical structure for an amino acid of Formula (II) formed when the amino acid of Formula (I) undergoes a deprotection step.
Figure 27:
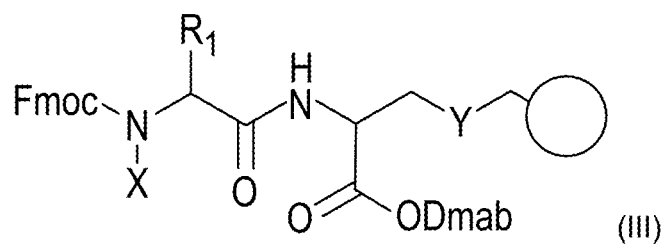
FIG. 27: Shows the chemical structure of a Fmoc-amino acid forming the compound of Formula (III).

Next, the amino acid Formula (I) undergoes a deprotection step producing the amino acid of Formula (II) as shown in FIG. 26:

Next, the compound of Formula (II) is coupled with an Fmoc-amino acid forming the compound of Formula (III) as shown in FIG. 27:
wherein:
X is H or Me;
R1 is an L or D amino acid, wherein said amino acid is a canonical amino acid or a non-canonical amino acid;
Y is an amino acid, and preferably an amino acid selected from the group consisting of: Ser, Thr, Asn, Gln, Asp, Glu, and Tyr; and
Dmab is:

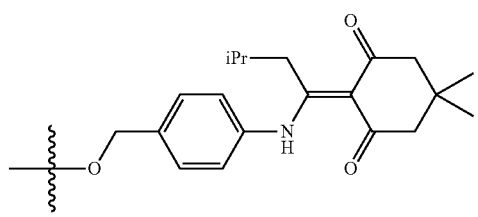 [SMILES: *OCc1ccc(NC(CC(C)C)=C2C(=O)CC(C)(C)CC2=O)cc1]

The deprotection and coupling steps may be optionally repeating extending said peptide to include peptides between a 1-mer to a 10-mer, or longer. In this embodiment, the extended peptide may be coupled with a Fmoc bullvalene amino acid (Fmoc-Bva) according to Formula (IV) as shown in FIG. 21 forming, in this instances a linear-resin bound peptide containing a bullvalene amino acid which may further be cyclized as described below.

wherein:
X is H or Me;
$R_1$-$R_4$ is an L or D amino acid, wherein said amino acid is a canonical amino acid or a non-canonical amino acid;
Y is an amino acid, and preferably an amino acid selected from the group consisting of: Ser, Thr, Asn, Gln, Asp, Glu, and Tyr;
Dmab is:

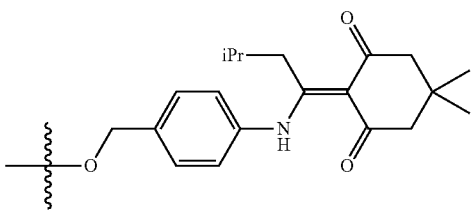 [SMILES: *OCc1ccc(NC(CC(C)C)=C2C(=O)CC(C)(C)CC2=O)cc1]

Figure 24:
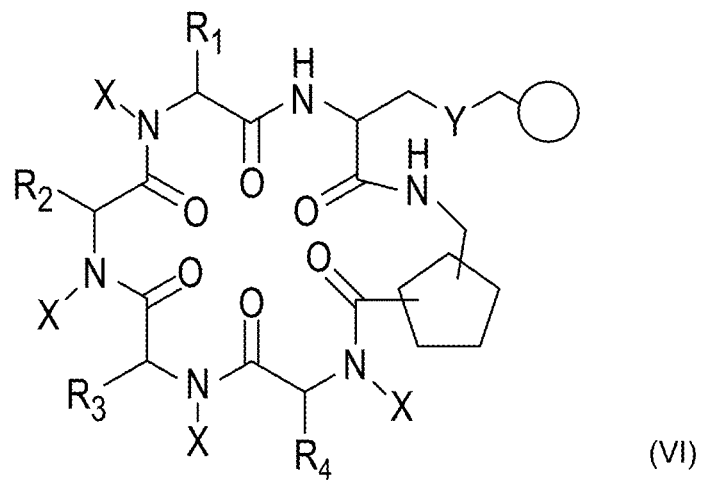
FIG. 24: An Fmoc bullvalene containing peptide may be cyclized to form a Shape Shifting Cyclic Peptides (SSCP), which may be synthesized by taking the Fmoc bullvalene containing peptide generally described in Formula (V) and initiating one or more rounds of deprotecting and cyclization forming a resin-bound Fmoc bullvalene containing cyclic peptide according to Formula VI.

As noted elsewhere, this embodiment shows a Fmoc bullvalene containing peptide as a 4-mer, this is exemplary only as the size and number of amino acids can be variable. This Fmoc bullvalene containing peptide may be cyclized to form a Shape Shifting Cyclic Peptides (SSCP). In this preferred embodiment, a SSCP may be synthesized by taking the Fmoc bullvalene containing peptide generally described in Formula (V) and initiating one or more rounds of deprotecting and cyclization forming a resin-bound Fmoc bullvalene containing cyclic peptide according to Formula VI as shown in FIG. 24:
wherein:
X is H or Me;
$R_1$-$R_4$ is an L or D amino acid, wherein said amino acid is a canonical amino acid or a non-canonical amino acid; and
Y is an amino acid, and preferably an amino acid selected from the group consisting of: Ser, Thr, Asn, Gln, Asp, Glu, and Tyr.

Finally, the Fmoc bullvalene containing cyclic peptide may be cleaved from its resin support forming shape shifting cyclic peptide (SSCP) according to generalized Formula (VII) shown in FIG. 23:
wherein:
X is H or Me;
$R_1$-$R_4$ is an L or D amino acid, wherein said amino acid is a canonical amino acid or a non-canonical amino acid; and Y is an amino acid, and preferably an amino acid selected from the group consisting of: Ser, Thr, Asn, Gln, Asp, Glu, and Tyr.

One or more of the SSCP may be directed to a target, or may exhibit a therapeutic action in a subject, and preferably a human. As a result, additional embodiments include the step of administering a therapeutically effective amount of a bullvalene containing peptide or cyclic peptide, such as a Shape Shifting Cyclic Peptide (SSCP).

As shown in FIG. 6, additional embodiments of the invention may include methods of identifying a therapeutic compound comprising the step of: (i) generating a bullvalene containing fluxional cyclic peptide; (ii) introducing said bullvalene containing fluxional cyclic peptide cellular thermal shift assay; (iii) determining the target engagement of said bullvalene containing fluxional cyclic peptide; and (iv) optionally introducing a non-fluxional containing cyclic peptide to said cellular thermal shift assay; and (v) comparing the target engagement of said bullvalene containing fluxional cyclic peptide and said non-fluxional containing cyclic peptide.

The invention may include a fluxional peptide library, and methods of creating the same. As used herein a "fluxional peptide library" describes a collection of peptides, and preferably cyclic peptides having one or more bullvalene amino acids (Bva) that a may be used to identify a target binding compound. Such systems and methods may be part of a larger system to identify novel therapeutic compounds, such as a therapeutic peptide compounds. In this preferred embodiment, a fluxional peptide library comprising a plurality of fluxional peptide library members may be generated according to the methods described herein. As noted above, this fluxional peptide library may include one, or a plurality of peptides having at least one or more bullvalene amino acids (Bva) and/or one or a plurality of Shape Shifting Cyclic Peptides (SSCP). Fluxional peptide library members may be screened for activity against one or more targets. In this step, one or more fluxional peptide library members may contact, or be positioned in proximity to a target or a truncated analogue thereof, the target or truncated analogue thereof comprising an biological active site. In this preferred embodiment, a target may include a protein optionally having one or more active sites, such as a protein epitope or moiety. One or more fluxional peptide library members may have affinity for the active site such that they can be identified, for example through binding assays or other methods affinity assays known in the art.

Having identified fluxional peptide library members having affinity for the active site, the members of the library may be deconvoluted. The term "deconvolution" means the process whereby the active molecule or molecules, such as a fluxional peptides in a library are identified, and may include methods such as: 1) deconvolution of libraries cleaved from the solid support; 2) recursive deconvolution; 3) positional scanning; 4) omission libraries; and 5) deconvolution of tethered combinatorial libraries as well as other deconvolution methods known in the art. These combinatorial libraries can be made as mixtures, sets of individual fluxional peptides or chemical structures generated in vitro, in vivo or in silico through the use of one or more computer software applications operating on a digital device.

In a preferred embodiment, the step of deconvoluting fluxional peptide library members with affinity for the active site may include one or more iterative steps that may identify one or more characteristics of the fluxional peptide library members that demonstrates binding affinity to the active site. Alternative embodiments may include one or more iterative steps that identify one or more characteristics of the target active site, as well as interactions between the fluxional peptide library members and active site, as well as predicted interactions between a stable peptide analog of a fluxional peptide library members and the active site.

In specific embodiments, the step of deconvoluting one or more fluxional peptide library members with affinity for the active site may include, but not be limited to: 1) identifying one or more pharmacophores of a fluxional peptide library member having affinity for the active site; 2) identifying the sequence of a fluxional peptide library member having affinity for the active site; 3) identifying the binding affinity of a fluxional peptide library member having affinity for the active site. In further embodiments the step of deconvoluting one or more fluxional peptide library members with affinity for the active site may include identify or characterizing the active site of a target, such target being, as noted above a protein or a truncated analog of a protein or other protein fragment.

The invention may include systems and methods of identifying a target binding compound in silico. In this embodiment, a computing system or digital device having a processor may be configured to execute one or more software executable applications that may render, in a digital or virtual manner, a digital fluxional peptide library comprising a plurality of digital fluxional peptide library members, such library members comprising preferably peptides having at least one or more bullvalene amino acids (Bva) and/or one or a plurality of Shape Shifting Cyclic Peptides (SSCP). In this embodiment, the various fluxional isomers of individual members of the library may be sequentially or simultaneously generated by the software application, and may further be contacted, in a digital or virtual environment, with a target or truncated analogue thereof comprising an active site, also generated in silico. Next, the software application may identify, in silico, a digital fluxional peptide library member with affinity for the active site, for example based on a pre-determined binding affinity threshold.

As noted above, the ability of the SSCP compounds of the current invention to acts as poly-pharmacophores allows for the generation of a stable peptide analog of a fluxional peptide library member that present the same or similar pharmacophore and also has affinity for the activity site. In the embodiment, a stable peptide analog may include a peptide in a stable or locked configuration, and preferably a cyclic configuration that is an analog of a fluxional peptide library member. In a preferred embodiment, the stable peptide analog may include canonical or non-canonical amino acids and may have the same or similar pharmacophore as the fluxional peptide library member, such that both compounds have activity towards the active site.

As can be seen, the present invention can be used to identify novel therapeutic compounds, such as therapeutic peptides based on stable peptide analogs of SSCP, as well as active sites on target proteins, the binding of which may produce a therapeutic effect. In this manner, the invention may include systems and methods of generating a therapeutic peptide, in vitro, in vivo, or in silico, comprising the steps of generating one or more stable peptide analogs of a fluxional peptide library member generated by the methods of any claim above.

As can be appreciated, some of the steps as herein described may be accomplished in some embodiments through any appropriate machine and/or device, such as a computer system or digital device resulting in the transformation of, for example data, data processing, data transformation, external devices, operations, and the like. It should also be noted that in some instance's software and/or software solution may be utilized to carry out the objectives of the invention and may be defined as software stored on a magnetic or optical disk or other appropriate physical computer readable media including wireless devices and/or smart phones. In alternative embodiments the software and/or data structures can be associated in combination with a computer or processor that operates on the data structure or utilizes the software. Further embodiments may include transmitting and/or loading and/or updating of the software on a computer perhaps remotely over the internet or through any other appropriate transmission machine or device, or even the executing of the software on a computer resulting in the data and/or other physical transformations as herein described.

Certain embodiments of the inventive technology may utilize a machine and/or device which may include a digital devices, such as a general purpose computer, a computer that can perform an algorithm, computer readable medium, software, computer readable medium continuing specific programming, a computer network, a server and receiver network, transmission elements, wireless devices and/or smart phones, internet transmission and receiving element; cloud-based storage and transmission systems, software updateable elements; computer routines and/or subroutines, computer readable memory, data storage elements, random access memory elements, and/or computer interface displays that may represent the data in a physically perceivable transformation such as visually displaying said processed data. In addition, as can be naturally appreciated, any of the steps as herein described may be accomplished in some embodiments through a variety of hardware applications including a keyboard, mouse, computer graphical interface, voice activation or input, server, receiver and any other appropriate hardware device known by those of ordinary skill in the art.

A "processor," "processor system," or "processing system" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location or have temporal limitations. For example, a processor can perform its functions in "real time," "offline," " in a "batch mode," etc. Portions of processing can be performed at different times and at different locations, by different (or the same) processing systems. A computer may be any processor in communication with a memory. The memory may be any suitable processor-readable storage medium, such as random-access memory (RAM), read-only memory (ROM), magnetic or optical disk, or other tangible media suitable for storing instructions for execution by the processor.

Particular embodiments may be implemented by using a programmed computer system or digital device, such as a general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

Definitions

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention. The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

It may be convenient or desirable to prepare, purify, and/or handle the active compound in the form of a prodrug. The term "prodrug", as used herein, pertains to a compound which, when metabolized (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include, but are not limited to, those wherein R is $C_{1-20}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999). For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

As used herein the singular forms "a", "an", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ± a range of up to 20%, up to 15%, up to 10%, up to 5%, or up to 4%, 3%, 2%, or 1% compared to the specifically recited value.

The term "compound," "active compound," or "composition," or "compound of the invention" includes all solvates, complexes, polymorphs, radiolabeled derivatives, tautomers, stereoisomers, and optical isomers of the bullvalene containing compounds, and in particular SSCP compounds generally described herein, and salts thereof, unless otherwise specified.

As used herein, the term "peptide" refers to a polymer of amino acids linked by amide bonds as is known to those of skill in the art. A peptide can be a polymer of 4, 5, 6, 7, 8, 9, 10, 15, 20, 25, 30, 35, 40, 45, 50, 55, 60, 65, 70, 75, 80, 85, 90, 95, 100 or more amino acids linked by covalent amide bonds. In some embodiments, the peptide is a polymer of 6 to 8, 8 to 10, 10 to 15, 10 to 20, 10 to 25, 10 to 30, 10 to 40, 10 to 50, or 25 to 25 amino acids linked by covalent amide bonds. In certain embodiments, the peptide is a polymer of 50 to 65, 50 to 75, 50 to 85, 50 to 95, 50 to 100, 75 to 100 amino acids linked by covalent amide bonds. As used herein, the term can refer to a single peptide chain linked by covalent amide bonds. The term can also refer to multiple peptide chains associated by non-covalent interactions such as ionic contacts, hydrogen bonds, Van der Waals contacts and hydrophobic contacts. Those of skill in the art will recognize that the term includes peptides that have been modified, for example by post-translational processing such as signal peptide cleavage, disulfide bond formation, glycosylation (e.g., N-linked glycosylation), protease cleavage and lipid modification (e.g., S-palmitoylation).

As used herein, "Fmoc" means a base-labile protecting group used in organic synthesis, and in particular a fluorenylmethoxycarbonyl protecting group.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-group s/substituents include alkyl groups, hydroxyl groups, alkoxy groups, acyloxy groups, mercapto groups, and aryl groups.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein. Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term 'amino' as used herein refers to the group —NH$_2$. The term "alkylamino" refers to amino groups where one or both hydrogen atoms are replaced by a hydrocarbon group Hc as described above, wherein the amino nitrogen "N" can be substituted by one or two Hc groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group Hc as described above, wherein the amino nitrogen "N" can be substituted by one or two Hc groups as set forth for alkoxy groups described above.

As used herein, "bullvalene" generally describes a small polycycle with 10 carbons and 10 hydrogens, that it has no permanent chemical structure as its bonds are constantly rearranging through a series of Cope rearrangements.

The term "amino acid" means naturally occurring and non-naturally occurring amino acids, as well as amino acid analogs and amino acid mimetics that function in a manner similar to naturally occurring amino acids. Naturally, coded amino acids include 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine) And pyrrolysine and selenocysteine. Amino acid analogs refer to compounds having the same basic chemical structure as naturally occurring amino acids, i.e., having an α-carbon combined with hydrogen, carboxyl, amino and R groups, examples being homoserine, norleucine, methionine sulfoxide, methionine methyl There is sulfonium. Such analogs have modified R groups (eg, norleucine) or have modified peptide backbones, but maintain the same basic chemical structure as naturally occurring amino acids. Amino acids can be referred to herein according to their generally known nomenclature (three letter representation or one letter representation; recommended by the IUPAC-IUB Biochemical Nomenclature Commission). Similarly, nucleotides can also be referred to as commonly used one letter codes.

As used herein, "canonical amino acid" refers to one of the 20 common naturally occurring amino acids. As used herein, "non-canonical amino acid" refers to any amino acid, modified amino acid, and/or amino acid analog that is not one of the 20 common naturally occurring amino acids, and may be referred to as non-naturally occurring amino acids. Reference to any amino acid include both L and D forms of the same. Additional embodiments of non-canonical amino acids may include pegylated and or fatty acid amino acids, as well as thalidomide, or analogs of thalidomide modification to one or more amino acids configured to generate Proteolysis Targeting Chimeras ("PROTAC") The term "Proteolysis Targeting Chimeras" or "PROTAC" refers to proteolysis-targeting chimera molecules having generally three components, an E3 ubiquitin ligase binding group (E3LB), a linker L2, and a protein binding group (PB). The terms "residue," "moiety" or "group" refers to a component that is covalently bound or linked to another component. For example, a "residue of a PROTAC" refers to a PROTAC that is covalently linked to one or more groups such as a Linker L2, which itself can be optionally further linked to an peptide.

As used herein the term "stable," with regard to the disclosed peptides or pharmaceutical formulation thereof means that the agent or formulation maintains structural and functional integrity for a sufficient period of time to be useful in the methods described herein.

As used herein, "analog" refers to a molecule that resembles another molecule in structure, such as a molecule which comprises a portion of the chemical structure or polymer sequence of another molecule, but which is not identical to or an isomer of such other molecule.

As used herein, "pharmaceutical composition" are compositions that include an amount (for example, a unit dosage) of one or more of the disclosed compounds, and preferably a SSCP as described herein, together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition). The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Such pharmaceutical compositions/formulations are useful for administration to a subject, in vivo or ex vivo. Pharmaceutical compositions and formulations include carriers or excipients for administration to a subject. As used herein the terms "pharmaceutically acceptable" and "physiologically acceptable" mean a biologically compatible formulation, gaseous, liquid, or solid, or mixture thereof, which is suitable for one or more routes of administration, in vivo delivery, or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules, and crystals. Supplementary active compounds (e.g., preservatives, antibacterial, antiviral, and antifungal agents) can also be incorporated into the compositions. The formulations may, for convenience, be prepared or provided as a unit dosage form. In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone. Supplementary active compounds (e.g., preservatives, antioxidants, antimicrobial agents including biocides and biostats such as antibacterial, antiviral, and antifungal agents) can also be incorporated into the compositions. Preservatives and other additives include, for example, antimicrobials, anti-oxidants, chelating agents, and inert gases (e.g., nitrogen). Pharmaceutical compositions may therefore include preservatives, antimicrobial agents, anti-oxidants, chelating agents, and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

Pharmaceutical compositions can optionally be formulated to be compatible with a particular route of administration. Exemplary routes of administration include administration to a biological fluid, an immune cell (e.g., T or B cell) or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles, or filling agents) suitable for administration to any cell, tissue, or organ, in vivo, ex vivo (e.g., tissue or organ transplant) or in vitro, by various routes and delivery, locally, regionally, or systemically.

Exemplary routes of administration for contact or in vivo delivery of a composition of the invention, is a dosage of the compound that is sufficient to achieve a desired therapeutic effect, such as can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and intralymphatic.

Formulations suitable for parenteral administration include aqueous and non-aqueous solutions, suspensions, or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable, or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils, or creams as generally known in the art.

For topical administration, for example, to skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof. An exemplary topical delivery system is a transdermal patch containing an active ingredient. For oral administration, pharmaceutical compositions include capsules, cachets, lozenges, tablets, or troches, as powder or granules. Oral administration formulations also include a solution or a suspension (e.g., aqueous liquid or a non-aqueous liquid; or as an oil-in-water liquid emulsion or a water-in-oil emulsion). For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient.

For airway or nasal administration, aerosol and spray delivery systems and devices, also referred to as "aerosol generators" and "spray generators," such as metered dose inhalers (MDI), nebulizers (ultrasonic, electronic, and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject. MDIs typically use liquid propellant and typically, MDIs create droplets that are 15 to 30 microns in diameter, optimized to deliver doses of 1 microgram to 10 mg of a therapeutic. Nebulizers are devices that turn medication into a fine mist inhalable by a subject through a face mask that covers the mouth and nose. Nebulizers provide small droplets and high mass output for delivery to upper and lower respiratory airways. Typically, nebulizers create droplets down to about 1 micron in diameter.

Dry-powder inhalers (DPI) can be used to deliver the compounds of the invention, either alone or in combination with a pharmaceutically acceptable carrier. DPIs deliver active ingredient to airways and lungs while the subject inhales through the device. DPIs typically do not contain propellants or other ingredients, only medication, but may optionally include other components. DPIs are typically breath-activated but may involve air or gas pressure to assist delivery.

Pharmaceutical formulations and delivery systems appropriate for the compositions and methods of the invention are known in the art (see, e.g., Remington: The Science and Practice of Pharmacy (2003) 20.sup.th ed., Mack Publishing Co., Easton, Pa.; Remington's Pharmaceutical Sciences (1990) 18.sup.th ed., Mack Publishing Co., Easton, Pa.; The Merck Index (1996) 12.sup.th ed., Merck Publishing Group, Whitehouse, N.J.; Pharmaceutical Principles of Solid Dosage Forms (1993), Technomic Publishing Co., Inc., Lancaster, Pa.; Ansel and Stoklosa, Pharmaceutical Calculations (2001) 11.sup.th ed., Lippincott Williams & Wilkins, Baltimore, Md.; and Poznansky et al., Drug Delivery Systems (1980), R. L. Juliano, ed., Oxford, N.Y., pp. 253-315).

In the methods of the invention, a SSCP, may be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly, or monthly. Timing of contact, administration ex vivo or in vivo delivery can be dictated by the, pathogenesis, symptom, pathology, or adverse side effect to be treated. For example, an amount can be administered to the subject substantially contemporaneously with, or within about 1-60 minutes or hours of the onset of a symptom or adverse side effect of treatment.

Doses may vary depending upon whether the treatment is therapeutic or prophylactic, the onset, progression, severity, frequency, duration, probability of or susceptibility of the symptom, the type of pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the, pathology or symptom, or any adverse side effects of the treatment or therapy. The skilled artisan will appreciate the factors that may influence the dosage, frequency and timing required to provide an amount sufficient or effective for providing a prophylactic or therapeutic effect or benefit.

Doses can be based upon current existing treatment protocols, empirically determined, determined using animal disease models or optionally in human clinical studies. A subject may be administered in single bolus or in divided/metered doses, which can be adjusted to be more or less according to the various consideration set forth herein and known in the art. Dose amount, frequency or duration may be increased or reduced, as indicated by the status of pathogenesis, associated symptom or pathology, or any adverse side effect(s). For example, once control or a particular endpoint is achieved, for example, reducing, decreasing, inhibiting, ameliorating, or preventing onset, severity, duration, progression, frequency, or probability of one or more symptoms associated with a telomere-associated disease or disorder.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

As used herein, "target" may be a target, such as a receptor or other molecule or structure, preferably in a human subject, such that inhibition or innervation of said target produces a therapeutic effect. Exemplary targets that are response to cyclic peptides include the CXCR4 receptor, GRB7, CK2a and Chymotrypsin.

As used herein, "therapeutically effective amount" of the disclosed compound, which may preferably be a SSCp, is a dosage of the compound that is sufficient to achieve a desired therapeutic effect or treatment.

As used herein, "therapeutic effect" as used herein in the context of treating a condition, refers to extended relieve of symptoms (duration) and/or a more significant reduction of symptoms (magnitude).

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, and particularly in a human, and includes: (a) preventing the disease from occurring in a subject which may be predisposed to the disease but has not yet been diagnosed as having it: (b) inhibiting the disease, i.e., arresting its development; (c) relieving the disease, i.e., causing regression of the disease; (d) protection from or relief of a symptom or pathology caused by the disease; (e) reduction, decrease, inhibition, amelioration, or prevention of onset, severity, duration, progression, frequency or probability of one or more symptoms or pathologies associated with the disease; and (f) prevention or inhibition of a worsening or progression of symptoms or pathologies associated with the disease.

The terms "individual," "subject," and "patient," used interchangeably herein, refer to a mammal, including, but not limited to, murines, simians, humans, mammalian farm animals, mammalian sport animals, and mammalian pets. Preferably, the subject herein is human.

As used herein, "analog of a cyclic peptide drug" comprise an analog of a known cyclic peptide that has a therapeutic effect, wherein said analog comprises at least one bullvalene containing amino acid.

Another embodiment of this disclosure provides pharmaceutical kits containing a pharmaceutical composition of this disclosure, and preferably a SSCP, prescribing information for the composition, and a container.

Each publication or patent cited herein is incorporated herein by reference in its entirety.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1: Scalable Production of Bullvalene Fmoc Amino Acids (Bva)

As noted above, despite bullvalene's history as a fluxional molecule, its synthesis has traditionally been beset by low yields, long step counts, or a combination of the two, particularly for molecules with 1 or more substitutions. As a result, bullvalene has remained a chemical peculiarity, with few chemists attempting to explore the possibilities of this powerful shapeshifting molecule. As shown in FIG. 2A, a general and high yielding 2-step synthesis of fluxional mono- and di-functional bullvalene molecules has been shown in the prior art using a cobalt(I)-catalyzed [6+2] cycloaddition reaction between cyclooctatetraene (COT, 1) and terminal or internal alkynes (2) to create a tetraene core (3) that could subsequently undergo photo-mediated di-π methane rearrangement to yield substituted bullvalenes (4). This 2-step method resulted in the straightforward synthesis of gram scale quantities of several bullvalene derivatives allowing further development of this potential compounds in directed applications.

Example 2: Synthesis of Di-Functional Bullvalene Amino Acids

Building on the direct and scalable approach to substituted bullvalenes described above, the present inventors investigated use of this reaction sequence to yield a heterodisubstituted bullvalene amino acid (Bva) for use in SPPS. As shown in FIG. 2B, the present inventors first decorated an Fmoc-protected propargyl amine (2a) to the heterosubstituted internal alkyne (2b) through a Cu(I)-catalyzed coupling reaction, however, subsequent Co(I)-catalyzed [6+2] cycloaddition resulted only in recovery of starting materials. Next, as shown in FIG. 2C the present inventors investigated the reaction of COT with 1,4-butynediol (2c) under reported Co(I)-catalyzed conditions to give tetraene 3a, albeit in poor yields and variable purities. Further synthetic elaboration of 3a through activation (top) or oxidation to dialdehyde 3b and subsequent modification (bottom) largely resulting in decomposed starting materials or intractable mixtures of products.

The present inventors reasoned that the Co(I)-catalyzed cycloaddition was incompatible with the sterics and electronics of internal alkynes (e.g., 2b and 2c). Given that intramolecular reactions can proceed 100,000× faster than similar intermolecular reactions, as shown in FIG. 2D, the present inventors hypothesized that the efficacy of the Co(I)-catalyzed cycloaddition could be enhanced if the COT and alkyne were connected intramolecularly through an amide tether (1a). Outside of intramolecularizing the reactants, this amide tether could be hydrolyzed following the cycloaddition to unveil the desired amino acid functionality (3c to 4a) if properly activated.

As shown in FIG. 2E, COT was first mono-brominated to 1b under reported conditions on large scales, then converted to a Grignard reagent and reacted with $CO_2$ to from acid 1c in good yields. Peptide coupling with propargyl amine (2d) under standard conditions and reaction with boc anhydride ($Boc_2O$) gave the decorated COT 1d ready for intramolecular cycloaddition. As further shown in FIG. 2E, the present inventors next proposed the following 3-step sequence to create the desired bullvalene amino acid: intramolecular Co(I)-catalyzed cycloaddition to yield 3d, ii) basic hydrolysis of the Boc-appended amide to furnish 3e, and, finally, iii) photo-induced di-π methane rearrangement in the presence of catalytic quantities of a triplet sensitizer (ITX) to the fluxional boc-protected bullvalene amino acid (4b). Functional group manipulation of 4b by deprotection of the Boc-group with acid to yield 4c, followed by reaction with N-(9-fluorenylmethoxycarbonyloxy)succinimide (Fmoc-OSu) under basic conditions provides the final desired Fmoc-Bva 4d.

Notably, previously reported low yields obtained by the di-π methane rearrangement of di- or tri-substituted bullvalenes can be overcome by rapid and small-scale optimization of the photochemical rearrangement using a carousel photoreactor), allowing up to 20 samples to be irradiated at once in standard 5 mm NMR tubes. Parameters such as solvent, triplet sensitizer, and dose can be optimized for yield and purity of the bullvalene product. Streamlining the synthesis by direct activation of amide 1d with Fmoc-OSu as opposed to $Boc_2O$ can also be used as an alternative synthesis route.

Example 3: Synthesis of Tri-Functional Bullvalene Amino Acids

Provided the modularity of the above detailed synthetic route, as shown in FIG. 3A, the present inventors anticipated that COT acid 1c could act as a divergent core molecule, undergoing facile amide coupling with internal alkynes based on propargyl amine (5), followed by reaction with $Boc_2O$ to yield additional tethered COT cores (1e). Further elaboration of cores 1e through the above 3-step process (Co(I)-catalyzed cycloaddition, hydrolysis, and di-π methane rearrangement) would yield various tri-substituted bullvalenes (4e). Given the chemoselectivity and mildness of the proposed sequence, as well as the possibility for the use of traditional side chain amino acid protecting groups, several canonical (5a-5g) and non-canonical (5h-5i) side chains may be generated. Outside of offering a wider array of accessible chemical and physical properties, tri-substituted bullvalenes (4e) will form a significantly larger library of structural isomers (30 to 240), increasing the potential library size.

Example 4: Synthesis of an In-Situ Locking Bva

Although it is anticipated that dynamic shapeshifting of substituted bullvalene amino acids may enable access to otherwise impossible topologies in cyclic peptides, continuously fluxional molecules will significantly complicate structural identification of a "hit". Therefore, temporal "locking" of shapeshifting through means of chemical conversion of bullvalene to a static core may have advantageous properties. As shown in FIG. 3C, such a "locked" configuration may be accomplished by the oxidation of a boronic acid containing bullvalene (e.g., 4f), derived from Bva-Bor developed in the previous sub-aim, to a static bullvalone (e.g., 4g). Here, a large ensemble of Bva-Bor containing cyclic peptides (240 isomers/cyclic peptide) can be fully fluxional until the addition of an excess hydrogen peroxide ($H_2O_2$), which will rapidly oxidize the boronic acid to an enone that spontaneously tautomerizes to a ketone (FIG. 3C). Locking of the library can only be after the library has been allowed to anneal to the target, significantly reducing the number of bullvalene isomers (240 to 30) and stopping any subsequent shapeshifting.

Example 5: Demonstration of Compatibility of Bva with Solid Phase Peptide Synthesis and Bva Fluxionality Through Production of Cyclic Peptide Analogs of Known Cyclic Peptide Drugs Small cyclic peptides are an ideal scaffold for inclusion of bullvalene as they are readily assembled with high chemical diversity, can be partitioned into cell permeable and non-permeable fractions, and importantly cyclic peptides have already been demonstrated to be effective drugs, with over 40 cyclic peptides currently in clinical use and one new cyclic peptide drug entering the market every year. As such, in one preferred embodiment outlined in FIG. 4, the present inventors demonstrate the compatibility of representative Bva's with standard SPPS and through the synthesis of a series of known cyclic peptide drugs as well as their Bva incorporated analogs. These may then be analyzed for their shape-shifting properties and ability to engage multiple targets besides the static peptide target described below.

Example 6: Stability of Bva Under Unitary SPPS Conditions

To assess the compatibility of Bva with SPPS conditions, one or more representative disubstituted Bva compounds may be subjected to each step of standard SPPS conditions for an extended period (96 hours) which corresponds to at least 80 cycles of SPPS. Because the target cyclic peptides are 5-9 amino acids in length this corresponds to 10 times the average synthesis time. The stability of Bva can be quantified by analytical NMR using the distinctive broad H1 NMR peak at ~5.8 ppm. For these studies, the previously prepared di-substituted bullvalene described in FIG. 4A (4h) may be used as a model Bva. This data may demonstrate the stability of the bullvalene core under unitary SPPS conditions of activation/coupling (N,N'-diisopropylcarbodiimide [DIC]/6-chloro-1-hydroxybenzotriazole Cl-HOBt in DMF) and deprotection (10% piperidine in DMF). Samples of the model Bva can be placed in NMR tubes along with the SPPS unitary reagents and deuterated DMSO and monitored by 1H-NMR at 1, 2, 4, 8, 16, 32, and 96 hours. The stability of the model Bva can further be quantified by integration of the broad ~5.8 ppm (corresponding to protons of bullvalene) over time.

Example 7: Maximum Number of SPPS Cycles for Which Bva is Stable and the Context Dependent Coupling Efficiencies of Bva In one embodiment, short 4-mer peptides may be prepared by sequential coupling of 1 alanine residue, each standard amino acid (20 total), Fmoc-Bva, and each standard amino acid (20 total). Finally, deprotection and capping with acetic anhydride may be performed. These capped and resin bound four-mers may then be subjected to multiple rounds of SPPS cycles followed by standard resin cleavage with TFA/TIS/water. The resultant product purity and yield can be determined for 1, 10, and 20 post-blocking cycles using HPLC. This data may further complement the stability data described above and provide confidence of the overall stability of Bva in SPPS as well as the relative coupling efficiencies of each amino acid before and after the Bva. Notably, Bva may have lower coupling efficiencies akin to beta-branched amino acids, as is seen in Val-Val couplings.

Example 8: Synthesize Bva Analogs of Known Cyclic Peptide Drugs

Bva may further be incorporated into Fmoc-solid phase peptide synthesis (SPPS) using well-established methods described generally in FIG. 4B-C. Here, the present inventors may take advantage of several cyclic peptide drugs for which 3D structures of the bound target are known and have been rigorously analyzed. As highlighted in FIG. 5, these include cyclic peptide drugs targeting the CXCR4 receptor, GRB7, CK2a and Chymotrypsin. This may allow the production of Bva analogs that can be tested and compared to the parent cyclic peptide with regards to binding and polypharmacology.

Example 9: Demonstration of the Fluxional Nature of the Bva Cyclic Peptides and Evaluation of a Cellular Thermal Shift Assay to Determine Target Engagement The fluxional nature of the Bva cyclic peptides produced through the methods described above may be analyzed using a cooled HPLC isolation method previously described in the art for bullvalene analogs to assess the fluxional nature and interconversion of isomers within the cyclic peptide backbone. Subsequently, a rapid cellular thermal shift assay may be used to explore the target engagement specificity of the parent cyclic peptides compared to the Bva substituted analogs. Specifically, to demonstrated their fluxional nature of Bva cyclic peptides, purified at elevated (60° C.) temperature may be cooled to 4° C. and analyzed by HPLC to determine the distribution of isomers. Subsequently a single isolated peak or an isolated region from the low temperature separation can be allowed to equilibrate at 37° C. and analyzed again by HPLC at 4° C. to examine the isomer redistribution dynamics.

As shown in FIG. 6, to further demonstrate the relative target engagement of parent and Bva cyclic peptides, the present inventors may employ a previously developed drug target assay that maps the proteome thermostability in the presence and absence of a drug compound to test the expected multiple target engagement together with the expected bone-fide target engagement in cells. This assay may be performed with the Bva inserted cyclic peptide as well as the non-fluxional parent cyclic peptide using both HEK and SKBM2 cells in one embodiment.

REFERENCES

1) Achard, M., Mosrin, M., Tenaglia, A., and Buono, G. (2006). Cobalt(I)-Catalyzed [6+2] Cycloadditions of Cyclooctatetra(tri)ene with Alkynes. J. Org. Chem. 71, 2907-2910.
2) Ault, A. (2001). The Bullvalene Story. The Conception of Bullvalene, a Molecule That Has No Permanent Structure. J. Chem. Educ. 78, 924.
3) Ayub, R., Papadakis, R., Jorner, K., Zietz, B., and Ottosson, H. (2017). Cyclopropyl Group: An Excited-State Aromaticity Indicator? Chem.—Eur. J. 23, 13684-13695.
4) Ball, K. A., Webb, K. J., Coleman, S. J., Cozzolino, K. A., Jacobsen, J., Jones, K. R., Stowell, M. H. B., and Old, W. M. (2020). An isothermal shift assay for proteome scale drug-target identification. Commun. Biol. 3, 75.
5) Baussanne, I., Travers, C., and Royer, J. (1998). Asymmetric synthesis of 3-substituted pyrrolidones via α-alkylation of a chiral non-racemic γ-lactam. Tetrahedron Asymmetry 9, 797-804.
6) Bittner, G. C. V. de, Dubikovskaya, E. A., Bertozzi, C. R., and Chang, C. J. (2010). In vivo imaging of hydrogen peroxide production in a murine tumor model with a chemoselective bioluminescent reporter. Proc. Natl. Acad. Sci. 107, 21316-21321.
7) Bohacek, R. S., McMartin, C., and Guida, W. C. (1996). The art and practice of structure-based drug design: a molecular modeling perspective. Med. Res. Rev. 16, 3-50.
8) He, M., and Bode, J. W. (2011). Racemization as a stereochemical measure of dynamics and robustness in shape-shifting organic molecules. Proc. Natl. Acad. Sci. 108, 14752-14756.
9) He, M., and Bode, J. W. (2013). E pluribus unum: isolation, structure determination, network analysis and DFT studies of a single metastable structure from a shapeshifting mixture of 852 bullvalene structural isomers. Org. Biomol. Chem. 11, 1306-1317.
10) Hewitt, W. M., Leung, S. S. F., Pye, C. R., Ponkey, A. R., Bednarek, M., Jacobson, M. P., and Lokey, R. S. (2015). Cell-Permeable Cyclic Peptides from Synthetic Libraries Inspired by Natural Products. J. Am. Chem. Soc. 137, 715-721.
11) Isidro-Llobet, A., Álvarez, M., and Albericio, F. (2009). Amino Acid-Protecting Groups. Chem. Rev. 109, 2455-2504.
12) Knowles, J. R., and Parsons, C. A. (1969). Proximity Effect in Catalysed Systems: a Dramatic Effect on Ester Hydrolysis. Nature 221, 53-54.
13) Lippert, A. R., Keleshian, V. L., and Bode, J. W. (2009). Dynamic supramolecular complexation by shapeshifting organic molecules. Org. Biomol. Chem. 7, 1529-1532.
14) Lippert, A. R., Naganawa, A., Keleshian, V. L., and Bode, J. W. (2010). Synthesis of Phototrappable Shape-Shifting Molecules for Adaptive Guest Binding. J. Am. Chem. Soc. 132, 15790-15799.
15) Malde, A. K., Hill, T. A., Iyer, A., and Fairlie, D. P. (2019). Crystal Structures of Protein-Bound Cyclic Peptides. Chem. Rev. 119, 9861-9914.

16) Patel, H. D., Tran, T.-H., Sumby, C. J., Pašteka, L. F., and Fallon, T. (2020). Boronate Ester Bullvalenes. J. Am. Chem. Soc. 142, 3680-3685.

17) Paul, S. M., Mytelka, D. S., Dunwiddie, C. T., Persinger, C. C., Munos, B. H., Lindborg, S. R., and Schacht, A. L. (2010). How to improve R&D productivity: the pharmaceutical industry's grand challenge. Nat. Rev. Drug Discov. 9, 203-214.

18) Rahman, M. M., Teng, J., Worrell, B. T., Noviello, C. M., Lee, M., Karlin, A., Stowell, M. H. B., and Hibbs, R. E. (2020). Structure of the Native Muscle-type Nicotinic Receptor and Inhibition by Snake Venom Toxins. Neuron 0.

19) Santos, R., Ursu, O., Gaulton, A., Bento, A. P., Donadi, R. S., Bologa, C. G., Karlsson, A., Al-Lazikani, B., Hersey, A., Oprea, T. I., et al. (2017). A comprehensive map of molecular drug targets. Nat. Rev. Drug Discov. 16, 19-34.

20) Schreiber, S. (2018). A chemical biology view of bioactive small molecules and a binder-based approach to connect biology to precision medicines. BioRxiv.

21) Suárez, A., and Fu, G. C. (2004). A Straightforward and Mild Synthesis of Functionalized 3-Alkynoates. Angew. Chem. Int. Ed. 43, 3580-3582.

22) Teichert, J. F., Mazunin, D., and Bode, J. W. (2013). Chemical Sensing of Polyols with Shapeshifting Boronic Acids As a Self-Contained Sensor Array. J. Am. Chem. Soc. 135, 11314-11321.

23) Yahiaoui, O., Pašteka, L. F., Judeel, B., and Fallon, T. (2018). Synthesis and Analysis of Substituted Bullvalenes (John Wiley & Sons, Ltd).

24) Yahiaoui, O., Pašteka, L. F., Blake, C. J., Newton, C. G., and Fallon, T. (2019). Network Analysis of Substituted Bullvalenes. Org. Lett. 21, 9574-9578.

25) Yan, L. Z., Edwards, P., Flora, D., and Mayer, J. P. (2004). Synthesis of cyclic peptides through hydroxyl side-chain anchoring. Tetrahedron Lett. 45, 923-925.

26) Zimmerman, H. E., and Armesto, D. (1996). Synthetic Aspects of the Di-π-methane Rearrangement. Chem. Rev. 96, 3065-3112.

27) Zorzi, A., Deyle, K., and Heinis, C. (2017). Cyclic peptide therapeutics: past, present and future. Curr. Opin. Chem. Biol. 38, 24-29.

What is claimed is:

1. A di-substituted bullvalene amino acid (Bva) composition according to Formula (I-A):

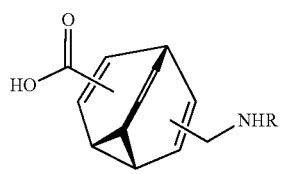

(I-A)

wherein R is H, a protecting group, Boc, or Fmoc.

2. A tri-substituted bullvalene amino acid (Bva) composition according to Formula (I-B):

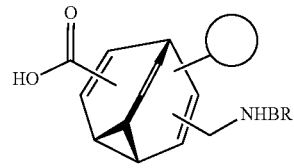

(I-B)

wherein R is H, a protecting group, Boc, or Fmoc; and wherein

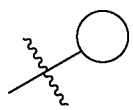

comprises a canonical and/or non-canonical side-chain optionally selected from the group consisting of:

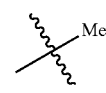

Bva-Ala

5a

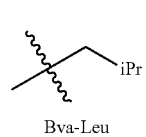

Bva-Leu

5b

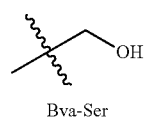

Bva-Ser

5c

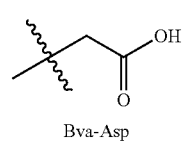

Bva-Asp

5d

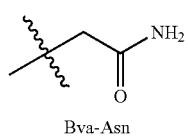

Bva-Asn

5e

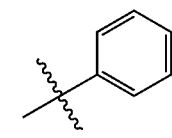

Bva-Phe

5f

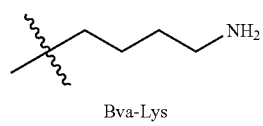

Bva-Lys

5g

-continued

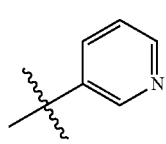

Bva-Pyr (5h)

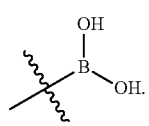

Bva-Bor (5i)

3. The composition of claim 1, wherein the composition comprises an Fmoc-Bva and is further incorporated into a Fmoc-solid phase peptide synthesis (SPPS) system forming a linear peptide coupled with said Fmoc-Bva which can be cyclized forming a Shape Shifting Cyclic Peptide (SSCP).

4. The composition of claim 2, wherein the composition comprises an Fmoc-Bva and is further incorporated into a Fmoc-solid phase peptide synthesis (SPPS) system forming a linear peptide coupled with said Fmoc-Bva which can be cyclized forming a Shape Shifting Cyclic Peptide (SSCP).

* * * * *